United States Patent
Streeter et al.

(10) Patent No.: US 8,025,687 B2
(45) Date of Patent: Sep. 27, 2011

(54) LOW LEVEL LIGHT THERAPY FOR ENHANCEMENT OF NEUROLOGIC FUNCTION

(75) Inventors: Jackson Streeter, Reno, NV (US); Luis DeTaboada, Carlsbad, CA (US)

(73) Assignee: PhotoThera, Inc., Carlsbad, CA (US)

( * ) Notice: Subject to any disclaimer, the term of this patent is extended or adjusted under 35 U.S.C. 154(b) by 168 days.

(21) Appl. No.: 12/435,274

(22) Filed: May 4, 2009

(65) Prior Publication Data

US 2009/0216301 A1   Aug. 27, 2009

Related U.S. Application Data

(63) Continuation of application No. 10/764,986, filed on Jan. 26, 2004, now Pat. No. 7,534,255.

(60) Provisional application No. 60/442,693, filed on Jan. 24, 2003, provisional application No. 60/487,979, filed on Jul. 17, 2003, provisional application No. 60/537,190, filed on Jan. 19, 2004.

(51) Int. Cl.
*A61N 5/06* (2006.01)
(52) U.S. Cl. .......................................... 607/88; 128/898
(58) Field of Classification Search .................. 128/898; 606/2–19; 607/88–94
See application file for complete search history.

(56) References Cited

U.S. PATENT DOCUMENTS

| | | | |
|---|---|---|---|
| 1,856,969 A | 5/1932 | Reiter et al. | |
| 3,735,755 A | 5/1973 | Eggleton et al. | |
| 3,810,367 A | 5/1974 | Peterson | |
| 4,315,514 A | 2/1982 | Drewes et al. | |
| 4,343,301 A | 8/1982 | Indech | |
| 4,535,784 A | 8/1985 | Rohlicek et al. | |
| 4,539,987 A | 9/1985 | Nath et al. | |
| 4,630,273 A | 12/1986 | Inoue et al. | |
| 4,633,872 A | 1/1987 | Chaffee et al. | |
| 4,669,466 A | 6/1987 | L'Esperance | |
| 4,671,285 A | 6/1987 | Walker | |
| 4,686,986 A | 8/1987 | Fenyo et al. | |
| 4,798,215 A | 1/1989 | Turner | |
| 4,836,203 A | 6/1989 | Muller et al. | |
| 4,846,196 A | 7/1989 | Wiksell et al. | |
| 4,850,351 A | 7/1989 | Herman et al. | |
| 4,930,504 A | 6/1990 | Diamantopoulos et al. | |

(Continued)

FOREIGN PATENT DOCUMENTS

EP    0 130 950    4/1990

(Continued)

OTHER PUBLICATIONS

EPO Extended Search Report re EP Application No. 09170679.6, dated Jan. 4, 2010 in 6 pages.

(Continued)

*Primary Examiner* — Henry M Johnson, III
(74) *Attorney, Agent, or Firm* — Knobbe, Martens, Olson & Bear, LLP (57) ABSTRACT

A method for treating a subject having Parkinson's disease or Alzheimer's disease is provided. The method includes non-invasively delivering light energy having a wavelength of about 630 nanometers to about 904 nanometers to the brain of the subject. Delivering the light energy can include (i) irradiating the scalp with light energy having an incident power density between about 10 mW/cm$^2$ to about 10 W/cm$^2$ and (ii) transmitting a portion of the light energy through the scalp and the skull to the brain, wherein the transmitted light energy has a power density of at least about 0.01 mW/cm$^2$ at a depth of approximately 2 centimeters below the dura.

11 Claims, 1 Drawing Sheet

U.S. PATENT DOCUMENTS

| | | |
|---|---|---|
| 4,951,482 A | 8/1990 | Gilbert |
| 4,951,653 A | 8/1990 | Fry et al. |
| 4,966,144 A | 10/1990 | Rochkind et al. |
| 4,998,930 A | 3/1991 | Lundahl |
| 5,029,581 A | 7/1991 | Kaga et al. |
| 5,037,374 A | 8/1991 | Carol |
| 5,047,006 A | 9/1991 | Brandston et al. |
| 5,054,470 A | 10/1991 | Fry et al. |
| 5,125,925 A | 6/1992 | Lundahl |
| 5,150,704 A | 9/1992 | Tatebayashi et al. |
| 5,259,380 A | 11/1993 | Mendes et al. |
| 5,265,598 A | 11/1993 | Searfoss et al. |
| 5,267,294 A | 11/1993 | Kuroda et al. |
| 5,282,797 A | 2/1994 | Chess |
| 5,358,503 A | 10/1994 | Bertwell et al. |
| 5,401,270 A | 3/1995 | Muller et al. |
| 5,441,495 A | 8/1995 | Liboff et al. |
| 5,445,146 A | 8/1995 | Bellinger |
| 5,445,608 A | 8/1995 | Chen et al. |
| 5,447,528 A | 9/1995 | Gerardo |
| 5,464,436 A | 11/1995 | Smith |
| 5,474,528 A | 12/1995 | Meserol |
| 5,501,655 A | 3/1996 | Roit et al. |
| 5,503,637 A | 4/1996 | Kyricos et al. |
| 5,511,563 A | 4/1996 | Diamond |
| 5,540,737 A | 7/1996 | Fenn |
| 5,580,550 A | 12/1996 | Gough et al. |
| 5,580,555 A | 12/1996 | Schwartz |
| 5,601,526 A | 2/1997 | Chapelon et al. |
| 5,616,140 A | 4/1997 | Prescott |
| 5,617,258 A | 4/1997 | Negus et al. |
| 5,621,091 A | 4/1997 | Kunkel et al. |
| 5,622,168 A | 4/1997 | Keusch et al. |
| 5,627,870 A | 5/1997 | Kopecky |
| 5,640,978 A | 6/1997 | Wong |
| 5,643,334 A | 7/1997 | Eckhouse et al. |
| 5,709,645 A | 1/1998 | Siever |
| 5,720,894 A | 2/1998 | Neev et al. |
| 5,728,090 A | 3/1998 | Martin et al. |
| 5,755,752 A | 5/1998 | Segal |
| 5,762,867 A | 6/1998 | D'Silva |
| 5,769,878 A | 6/1998 | Kamei |
| 5,817,008 A | 10/1998 | Rafert et al. |
| 5,824,024 A | 10/1998 | Dial |
| 5,842,477 A | 12/1998 | Naughton et al. |
| 5,843,073 A | 12/1998 | Sinofsky |
| 5,849,585 A | 12/1998 | Mather et al. |
| 5,871,521 A | 2/1999 | Kaneda et al. |
| 5,879,376 A | 3/1999 | Miller |
| 5,902,741 A | 5/1999 | Purchio et al. |
| 5,928,207 A | 7/1999 | Pisano et al. |
| 5,928,945 A | 7/1999 | Seliktar et al. |
| 5,951,596 A | 9/1999 | Bellinger |
| 5,954,762 A | 9/1999 | Di Mino et al. |
| 5,958,761 A | 9/1999 | Yogev et al. |
| 5,983,141 A | 11/1999 | Sluijter et al. |
| 5,989,245 A | 11/1999 | Prescott |
| 6,030,767 A | 2/2000 | Wagner et al. |
| 6,033,431 A | 3/2000 | Segal |
| 6,042,531 A | 3/2000 | Holcomb |
| 6,045,575 A | 4/2000 | Rosen et al. |
| 6,046,046 A | 4/2000 | Hassanein |
| 6,060,306 A | 5/2000 | Flatt et al. |
| 6,063,108 A | 5/2000 | Salansky et al. |
| 6,100,290 A | 8/2000 | Levy et al. |
| 6,107,325 A | 8/2000 | Chan et al. |
| 6,107,608 A | 8/2000 | Hayes |
| 6,112,110 A | 8/2000 | Wilk |
| 6,117,128 A | 9/2000 | Gregory |
| 6,129,748 A | 10/2000 | Kamei |
| 6,143,878 A | 11/2000 | Koopman et al. |
| 6,146,410 A | 11/2000 | Nagypal et al. |
| 6,149,679 A | 11/2000 | Di Mino et al. |
| 6,156,028 A | 12/2000 | Prescott |
| 6,162,211 A | 12/2000 | Tankovich et al. |
| 6,179,771 B1 | 1/2001 | Mueller |
| 6,179,830 B1 | 1/2001 | Kokubu |
| 6,187,210 B1 | 2/2001 | Lebouitz et al. |
| 6,198,958 B1 | 3/2001 | Ives et al. |
| 6,210,317 B1 | 4/2001 | Bonlie |
| 6,210,425 B1 | 4/2001 | Chen |
| 6,214,035 B1 | 4/2001 | Streeter |
| 6,221,095 B1 | 4/2001 | Van Zuylen et al. |
| 6,233,480 B1 | 5/2001 | Hochman et al. |
| 6,267,780 B1 | 7/2001 | Streeter |
| 6,273,885 B1 | 8/2001 | Koop et al. |
| 6,273,905 B1 | 8/2001 | Streeter |
| 6,277,974 B1 | 8/2001 | Lo et al. |
| 6,290,713 B1 | 9/2001 | Russell |
| 6,290,714 B1 | 9/2001 | Streeter |
| 6,306,130 B1 | 10/2001 | Anderson et al. |
| 6,312,451 B1 | 11/2001 | Streeter |
| 6,344,050 B1 | 2/2002 | Chen |
| 6,358,272 B1 | 3/2002 | Wilden |
| 6,363,285 B1 | 3/2002 | Wey |
| 6,364,907 B1 | 4/2002 | Obochi et al. |
| 6,379,295 B1 | 4/2002 | Woo |
| 6,395,016 B1 | 5/2002 | Oron et al. |
| 6,397,107 B1 | 5/2002 | Lee et al. |
| 6,402,678 B1 | 6/2002 | Fischell et al. |
| 6,421,562 B1 | 7/2002 | Ross |
| 6,436,094 B1 | 8/2002 | Reuter |
| 6,443,974 B1 | 9/2002 | Oron et al. |
| 6,443,977 B1 | 9/2002 | Jaillet |
| 6,443,978 B1 | 9/2002 | Zharov |
| 6,447,537 B1 | 9/2002 | Hartman |
| 6,471,716 B1 | 10/2002 | Pecukonis |
| 6,494,900 B1 | 12/2002 | Salansky et al. |
| 6,511,475 B1 | 1/2003 | Altshuler et al. |
| 6,514,220 B2 | 2/2003 | Melton, Jr. et al. |
| 6,537,301 B1 | 3/2003 | Kamei |
| 6,537,304 B1 | 3/2003 | Oron |
| 6,551,308 B1 | 4/2003 | Muller et al. |
| 6,554,853 B2 | 4/2003 | Chen |
| 6,571,735 B1 | 6/2003 | Wilkinson |
| 6,602,274 B1 | 8/2003 | Chen |
| 6,602,275 B1 | 8/2003 | Sullivan |
| 6,645,230 B2 | 11/2003 | Whitehurst |
| 6,663,659 B2 | 12/2003 | McDaniel |
| 6,676,655 B2 | 1/2004 | McDaniel |
| 6,689,062 B1 | 2/2004 | Mesallum |
| 6,692,486 B2 | 2/2004 | Jaafar et al. |
| 6,743,222 B2 | 6/2004 | Durkin et al. |
| 6,746,473 B2 | 6/2004 | Shanks et al. |
| 6,860,896 B2 | 3/2005 | Leber et al. |
| 6,866,678 B2 | 3/2005 | Shenderova et al. |
| 6,872,221 B2 | 3/2005 | Lytle |
| 6,896,693 B2 | 5/2005 | Sullivan |
| 6,899,723 B2 | 5/2005 | Chen |
| 6,902,563 B2 | 6/2005 | Wilkens et al. |
| 6,918,922 B2 | 7/2005 | Oron |
| 6,921,413 B2 | 7/2005 | Mahadevan-Jansen et al. |
| 6,974,224 B2 | 12/2005 | Thomas-Benedict |
| 7,041,094 B2 | 5/2006 | Connors et al. |
| 7,054,676 B2 | 5/2006 | Hedlund et al. |
| 7,066,929 B1 | 6/2006 | Azar et al. |
| 7,090,691 B2 | 8/2006 | Simkin et al. |
| 7,101,384 B2 | 9/2006 | Benedict |
| 7,118,563 B2 | 10/2006 | Weckwerth et al. |
| 7,150,710 B2 | 12/2006 | Haber et al. |
| 7,217,266 B2 | 5/2007 | Anderson et al. |
| 7,288,108 B2 | 10/2007 | DiMauro et al. |
| 7,303,578 B2 | 12/2007 | De Taboada et al. |
| 7,309,348 B2 | 12/2007 | Streeter et al. |
| 7,316,922 B2 | 1/2008 | Streeter |
| 7,344,555 B2 | 3/2008 | Anders et al. |
| 7,351,252 B2 | 4/2008 | Altshuler et al. |
| 7,351,253 B2 | 4/2008 | DiMauro et al. |
| 7,389,776 B2 | 6/2008 | Maksimovich |
| 7,463,916 B2 | 12/2008 | Kawasaki et al. |
| 7,534,255 B1 | 5/2009 | Streeter et al. |
| 7,559,945 B2 | 7/2009 | Breden et al. |
| 7,575,589 B2 | 8/2009 | De Taboada et al. |
| 7,695,504 B2 | 4/2010 | Anders et al. |
| 7,744,590 B2 | 6/2010 | Eells et al. |
| 7,848,035 B2 | 12/2010 | Delapp et al. |
| 2001/0044623 A1 | 11/2001 | Chen |

| | | |
|---|---|---|
| 2002/0029071 A1 | 3/2002 | Whitehurst |
| 2002/0068927 A1 | 6/2002 | Prescot |
| 2002/0087205 A1 | 7/2002 | Chen |
| 2002/0099295 A1 | 7/2002 | Gil et al. |
| 2002/0123781 A1 | 9/2002 | Shanks et al. |
| 2002/0156371 A1 | 10/2002 | Hedlund et al. |
| 2002/0161418 A1 | 10/2002 | Wilkens et al. |
| 2002/0216797 | 10/2002 | Wilkens et al. |
| 2002/0188334 A1 | 12/2002 | Calgren |
| 2002/0198575 A1 | 12/2002 | Sullivan |
| 2003/0004556 A1 | 1/2003 | McDaniel |
| 2003/0021124 A1 | 1/2003 | Elbrecht et al. |
| 2003/0023283 A1 | 1/2003 | McDaniel |
| 2003/0109906 A1 | 6/2003 | Streeter |
| 2003/0125782 A1 | 7/2003 | Streeter |
| 2003/0125783 A1 | 7/2003 | Moran |
| 2003/0144712 A1 | 7/2003 | Streeter |
| 2003/0167080 A1 | 9/2003 | Hart et al. |
| 2003/0181961 A1 | 9/2003 | Kamei |
| 2003/0181962 A1 | 9/2003 | Streeter |
| 2003/0212442 A1 | 11/2003 | Streeter |
| 2003/0216797 A1 | 11/2003 | Oron |
| 2004/0010300 A1 | 1/2004 | Masotti et al. |
| 2004/0014199 A1 | 1/2004 | Streeter |
| 2004/0015214 A1 | 1/2004 | Simkin et al. |
| 2004/0030325 A1 | 2/2004 | Cahir et al. |
| 2004/0044384 A1 | 3/2004 | Leber et al. |
| 2004/0073278 A1 | 4/2004 | Pachys |
| 2004/0082862 A1 | 4/2004 | Chance |
| 2004/0093042 A1 | 5/2004 | Altshuler et al. |
| 2004/0132002 A1 | 7/2004 | Streeter |
| 2004/0138727 A1 | 7/2004 | Taboada et al. |
| 2004/0153130 A1 | 8/2004 | Oron et al. |
| 2004/0153131 A1 | 8/2004 | Yorke |
| 2004/0162596 A1 | 8/2004 | Altshuler et al. |
| 2004/0220513 A1 | 11/2004 | Streeter |
| 2004/0236226 A1 | 11/2004 | Maki et al. |
| 2004/0260367 A1 | 12/2004 | Taboada et al. |
| 2005/0005626 A1 | 1/2005 | McMahon |
| 2005/0009161 A1 | 1/2005 | Streeter |
| 2005/0024853 A1 | 2/2005 | Thomas-Benedict |
| 2005/0107851 A1 | 5/2005 | De Taboada et al. |
| 2005/0143792 A1 | 6/2005 | Jay |
| 2005/0159793 A1 | 7/2005 | Streeter |
| 2005/0187595 A1 | 8/2005 | Streeter |
| 2005/0203595 A1 | 9/2005 | Oron |
| 2005/0216072 A1 | 9/2005 | Mahadevan-Jansen et al. |
| 2006/0155348 A1 | 7/2006 | deCharms |
| 2006/0223155 A1 | 10/2006 | Streeter |
| 2006/0253177 A1 | 11/2006 | De Taboada et al. |
| 2007/0129778 A1 | 6/2007 | Dougal |
| 2007/0162093 A1 | 7/2007 | Porter et al. |
| 2007/0179570 A1 | 8/2007 | De Taboada et al. |
| 2007/0288072 A1 | 12/2007 | Pascual-Leone et al. |
| 2008/0004565 A1 | 1/2008 | Streeter et al. |
| 2008/0033412 A1 | 2/2008 | Whelan et al. |
| 2008/0033513 A1 | 2/2008 | Man et al. |
| 2008/0051858 A1 | 2/2008 | Haber et al. |
| 2008/0077199 A1 | 3/2008 | Shefi et al. |
| 2008/0125836 A1 | 5/2008 | Streeter et al. |
| 2008/0139941 A1 | 6/2008 | Njemanze |
| 2008/0140164 A1 | 6/2008 | Oberreiter et al. |
| 2008/0221211 A1 | 9/2008 | Streeter |
| 2008/0287930 A1 | 11/2008 | Rapoport |
| 2008/0312715 A1 | 12/2008 | Asirvatham et al. |
| 2009/0054955 A1 | 2/2009 | Kopell et al. |
| 2009/0088680 A1 | 4/2009 | Aravanis et al. |
| 2009/0112280 A1 | 4/2009 | Wingeier et al. |
| 2009/0163982 A1 | 6/2009 | deCharms |
| 2009/0222067 A1 | 9/2009 | Toselli et al. |
| 2009/0254154 A1 | 10/2009 | De Taboada et al. |
| 2009/0270776 A1 | 10/2009 | Chang |
| 2010/0010592 A1 | 1/2010 | De Taboada et al. |
| 2010/0010594 A1 | 1/2010 | De Taboada |
| 2010/0016841 A1 | 1/2010 | De Taboada |
| 2010/0094384 A1 | 4/2010 | De Taboada |
| 2010/0105977 A1 | 4/2010 | De Taboada et al. |
| 2010/0152820 A1 | 6/2010 | Anders et al. |
| 2010/0161017 A1 | 6/2010 | Choi et al. |
| 2010/0204762 A1 | 8/2010 | De Taboada et al. |
| 2010/0211136 A1 | 8/2010 | De Taboada et al. |
| 2011/0060266 A1 | 3/2011 | Streeter et al. |
| 2011/0102916 A1 | 5/2011 | DeLapp |

FOREIGN PATENT DOCUMENTS

| | | |
|---|---|---|
| EP | 0 763 371 A2 | 3/1997 |
| EP | 0 783 904 A2 | 7/1997 |
| EP | 1 074 275 | 2/2001 |
| EP | 1 226 787 A2 | 7/2002 |
| JP | 04023634 | 2/1992 |
| WO | WO 92/03964 | 3/1992 |
| WO | WO 96/36397 | 11/1996 |
| WO | WO 96/36396 | 1/1997 |
| WO | WO 98/04321 | 2/1998 |
| WO | WO 98/22573 | 5/1998 |
| WO | WO 99/42178 | 8/1999 |
| WO | WO 99/46005 | 9/1999 |
| WO | WO 99/62599 | 12/1999 |
| WO | WO 00/25684 | 5/2000 |
| WO | WO 00/35534 | 6/2000 |
| WO | WO 02/055149 | 7/2002 |
| WO | WO 02/064084 A2 | 8/2002 |
| WO | WO 02/092509 | 11/2002 |
| WO | WO 02/098509 | 12/2002 |
| WO | WO 2004/022154 A2 | 3/2004 |
| WO | WO 2005/118067 A1 | 12/2005 |
| WO | WO 2006/024038 A2 | 3/2006 |
| WO | WO 2006/105254 | 10/2006 |
| WO | WO 2006/115761 | 11/2006 |
| WO | WO 2006/138659 | 12/2006 |
| WO | WO 2008/049905 | 5/2008 |
| WO | WO 2008/141296 | 11/2008 |
| WO | WO 2009/067323 A1 | 5/2009 |
| WO | WO 2010/009452 A1 | 1/2010 |
| WO | WO 2010/031777 | 3/2010 |

OTHER PUBLICATIONS

U.S. Appl. No. 10/448,262, filed May 29, 2003, Oron et al.
U.S. Appl. No. 10/723,171, filed Nov. 26, 2003, Streeter.
Agov, B. S., et al., "On the mechanism of therapeutic action of helium-neon laser in ischemic heart disease", *Klin Med* (Mosc), pp. 102-105, 1985.
Arvidsson, Andreas, et al., "Neuronal replacement from endogenous precursors in the adult rat brain after stroke", *Nature Medicine*, vol. 8, No. 9, Sep. 2002, pp. 963-970.
Asahi, Minoru, et al., Expression of Interleukin B Converting Enzyme Gene Family and bcl-2 Gene Family in the Rat Brain Following Permanent Occlusion of the Middle Cerebral Artery, *Journal of Cerebral Blood Flow & Metabolism*, vol. 17, No. 1, Jan. 1997.
Assia, E. et al., "Temporal Parameters of Low Energy Laser Irradiation for Optimal Delay of Post-Traumatic Degeneration of Rat Optic Nerve", Brain Research, vol. 476, 1989, pp. 205-212.
Basford, Jeffrey R., M.D., Ph.D., "Lasers in Orthopedic Surgery—Laser Therapy: Scientific Basis and Clinical Role", May 1993, vol. 16, No. 5,pp. 541-547.
Belkin, M. et al., "A Critical Review of Low Energy Laser Bioeffects", Lasers and Light in Ophthalmology, vol. 2, No. 1, pp. 63-71, 1988.
Bevilacqua et al.; "In Vivo Local Determiniation of Tissue Optical Properties: Applications to the Human Brain"; *Applied Optics;* vol. 28, No. 22; Aug. 1, 1999; pp. 4939-4950.
Bibikova, A. et al., "Enhancement of Muscle Regeneration in the Toad (*Bufo viridis*) Gastrocnemius Muscle by Low-Energy Laser Irradiation", The Anatomical Reocrd, vol. 235, 1993, pp. 374-380.
Bibikova, A. et al., "Enhancement of Angiogenesis in Regenerating Gastroenemius Muscle of the Toad (*Bufo viridis*) by Low-Energy Laser Irradiation", Anatomy and Embryology (1994), vol. 190, pp. 597-602.
Brazzle, John, et al., Active Microneedles with Integrated Functionality, *Technical Digest of the 2000 Solid-State Sensor and Actuator Workshop,* Department of Bioengineering, University of Utah, Salt Lake City, Utah 84112 (five pages) (2000).
Brill, G.E., et al., Modifying influence of low level laser irradiation on the relationships in endothelial cell—blood platelet system, *10th Congress of the European Society for Photobiology,* Vienna, Austria (one page). Jun. 8, 2004.

Byrnes, K.R., et al., Light Therapy Promotes Axonal Regeneration After Acute Spinal Cord Injury in Adult Rats, Program No. 275.2, *Society for Neuroscience*, 2003, Abstract.

Chance et al.: "Comparison of Time-Resolved and -Unresolved Measurements of Deoxyhemoglobin in Brain"; *Proc. Natl Acad. Sc.i USA*; vol. 85; Jul. 1988; pp. 4971-4975.

Cohen, Michael A., Method of Forming Microneedles and other Micron-Scale Transdermal Probes, Office of Technology Licensing, University of California, Berkeley, http://otl.berkeley.edu/technology/inventiondetail. Php/1000335, Abstract (two pages) Dec. 5, 2003.

Conlan, M.J. et al., Biostimulation of Wound Healing by Low-Energy Laser Irradiation:, Journal of Clin. Periodontology, vol. 23, 1996, pp. 492-496.

Dirnagl, Ulrich, et al., Pathobiology of ischaemic stroke: an integrated view, *TINS*, vol. 22, No. 9, 1999, pp. 391-397.

Dobson, J., et al., Theory and Applications of a Magnetic Force Bioreactor, *European Cells and Materials*, vol. 4, Suppl. 2, 2002 (pp. 42-44).

Eells, J.T., et al., Therapeutic photobiomodulation for methanol-induced retinal toxicity, *Proceedings National Academy of Science (PNAS)*, vol. 100, No. 6, Mar. 18, 2003, pp. 3439-3444.

Elimadi, Aziz, et al., Trimetazidine Counteracts the Hepatic Injury Associated with Ischemia-Reperfusion by Michondrial Function, *Journal of Phamacology and Experimental Therapeutics*, vol. 286, No. 1, 1998, pp. 23-28.

Firbank et al.; "A Theoretical Study of the Signal Contributions of Regions of the Adult Head to Near-Infrared Spectroscopy Studies of Visual Evoked Responses"; *Neuroimage*; No. 8; 1998; pp. 69-78.

Fisher, M., "Characterizing the Target of Acute Stroke Therapy", Stroke, 1997, vol. 28, pp. 866-872.

Gage, Fred H., Brain, Repair Yourself, *Scientific American*, Sep. 2003, pp. 47-53.

Gasparyan, Levon V., Biochemical and Biophysical Effects of Low Level Laser Irradiation, *MAL 2000*, Helsinki, Finland (three pages), Sep. 28-30, 2000.

Gasparyan, Levon V., et al., Low Level Laser Therapy of Male Genital Tract Chronic Inflammations, *WALT 2-nd Congress* (Kansas City, USA), 1998 (two pages).

Gasparyan, Levon V., et al., The influence of LED irradiation at different wavelengths on functional activity of blood platelets, *10th Congress of the European Society of Photobiology*, Vienna, Austria, 2003 (one page).

Gasparyan, Levon V., et al., The influence of LED irradiation at different wavelengths with antioxidants on functional activity of blood platelets, Laser, Florence, 2003 (one page).

Gasparyan, Levon V., Experience of Russian (former USSR) Scientists in LLLT and UV Blood Irradiation, *MAL 2000*, Helsinki, Finland (four pages), Sep. 28-30, 2000.

Gasparyan, Levon V., Investigation of Sensations, Associated with Laser Blood Irradiation, *WALT 2-nd Congress* (Kansas City, USA), 1998 (two pages).

Gasparyan, Levan V., Millimeter Wave Therapy, *MAL 2000*, Helsinki, Finland (three pages). Sep. 28-30, 2000.

Gordon, G. A., "The Use of low power lasers in sports medicine", *Clinical Sports Medicine 2*, 53-61 (1990).

Gross, Garrett J., et al., Mechanisms of Postischemic Contractile Dysfunction, Myocardial Protection From Surgical Ischemic-Reperfusion Injury, *An International Symposium*, Asheville, North Carolina, Sep. 21-24, 1997, pp. 1898-1904.

Iadecola, Costantino, et al., Inhibition of inducible nitric oxide synthase ameliorates ischemic damage, *Am. J. Physiol.*, vol. 268, 1995, pp. R286-R292.

Karu, T.I., Low power laser therapy, in *Biomedical Photonics Handbook*, Ch. 48, Editor-in-Chief Tuan Vo-Dinh, Boca Raton, CRC Press, 2003.

Karu, Tiina, Mechanisms of interaction of monochromatic visible light with cells, *Proc. SPIE*, vol. 2630, pp. 2-9, 1996.

Karu, Tiina, Mechanisms of Low-Power Laser Light Action on Cellular Level, Effects of Low-Power Light on Biological Systems V, *Proceedings of SPIE*, Jul. 7, 2000, vol. 4159 pp. 1-17.

Karu, Tiina, Photobiological Fundamentals of Low Power Laser Therapy, *IEEE Journal of Quantum Electronics*, vol. QE-23, No. 10, Oct. 1987, pp. 1703-1717.

Karu, et al., Biostimulation of HeLa Cells by Low-Intensity Visible Light. II. Stimulation of DNA and RNA Synthesis in a Wide Spectral Range. Il Nuovo Cimento. (1984) p. 309-318.

Laser Exchange: Delivering the medicine of the future, http://www.laserexchange.co.uk/laser-therapy/ultrasound.htm; 42 pages, Oct. 13, 2004.

Leung, Mason C.P., et al., Treatment of Experimentally Induced Transient Cerebral Ischemia with Low Energy Laser Inhibits Nitric Oxide Synthase Activity and Up-Regulates the Expression of Transforming Growth Factor-Beta 1, *Laser in Surgery and Medicine*, 31:283-288 (2002).

Lychagov, Vladislav V., et al. Experimental study of NIRtransmittance of the human skull, *Proc. of SPIE*, vol. 6085, 2006 (five pages).

Mester, E., et al., Effect of Laser Rays on Wound Healing, *The American Journal of Surgery*, vol. 122, Oct. 1971, pp. 532-535.

Mochizuki-Oda, Noriko, et al., Effects of near-infra-red laser irradiation on adenosine triphosphate and adenosine diphosphate contents of rat brain tissue, *Neuroscience Letters 323*, May 3, 2002, pp. 207-210.

Nishioka, Norman S., et al., Reflection and Transmission of Laser Light From the Esophagus: The Influence of Incident Angle, *Gastroenterology*, vol. 94, 1988, pp. 1180-1185.

Nissan, M. et al., "HeNe Laser Irradiation Delivered Transcutaneously: Its Effect on the Sciatic Nerve of Rats", Lasers in Surgery and Medicine, vol. 6, pp. 435-438, 1986.

Olesin, Al, et al., Laser irradiation of venous blood for production of reperfusion syndrome in myocardial infarction, *Patologisheskaia fiziologiia*, 1992 (Abstract only).

Oron, Uri, et al., Attenuation of Infarct Size in Rats and Dogs after Myocardial Infarction by Low-Energy Laser Irradiation, *Lasers in Surgery and Medicine*, vol. 28, 2001, pp. 204-211.

Oron, Uri, et al., Low-Energy Laser Irradiation Reduces Formation of Scar Tissue After Myocardial Infarction in Rats and Dogs, Circulation, vol. 103, Jan. 16, 2001, pp. 296-301.

Park, James L., Ph.D., et al., Mechanisms of Myocardial Reperfusion Injury, The Annals of Thoracic Surgery, *Official Journal of Thoracic Surgeons and the Southern Thoracic Surgical Association*, vol. 68, No. 5, Nov. 1999, pp. 1905-1912.

International Search Report for PCT/CA99/00156, dated Jun. 11, 1999.

International Search Report and Written Opinion for PCT/US2007/002219, dated Jul. 5, 2007.

International Preliminary Report on Patentability for PCT/US2007/002219, dated May 2, 1998.

International Search Report and Written Opinion for PCT/US2007/002474, dated Sep. 27, 2007.

International Preliminary Report on Patentability for PCT/US2007/002474, dated Apr. 16, 2008.

International Search Report for PCT/US02/36808, dated Apr. 2, 2003.

International Search Report for PCT/US03/00747, dated May 14, 2003.

International Preliminary Report on Patentability for PCT/US04/029724, dated Mar. 23, 2006.

International Preliminary Report on Patentability for PCT/US2005/004873, dated Sep. 14, 2006.

International Search Report and Written Opinion for PCT/US2005/004873, dated Sep. 5, 2005.

Physical Therapy, The Efficacy of Laser Therapy for Musculoskeletal and Skin Disorders: A Criteria-Based Metanalysis of Randomized Clinical Trials, vol. 72, No. 7, Jul. 1992, pp. 483/12-491/21.

Pogue et al.: "Comparison of Image Geometries for Diffuse Optical Tomography of Tissue"; *Optics Express*; vol. 4, No. 8; Apr. 12, 1999; pp. 270-286.

Semenza, Gregg L., et al., Regulation of Mammalian O2 Homeostatis by Hypoxia-inducible Factor 1, *Ann. Rev. Cell Dev. Biol.*, vol. 15, 1999, pp. 551-578.

Smith, Kendric C., "The Photobiological Basis of Low Level Laser Radiation Therapy", *Photobiological Basis of LLLT*, pp. 1-7, 1991.

Stys, Peter K., Anoxis and Ischemic Injury of Myelinated Axons in CNS White Matter: From Mechanistic Concepts to Therapeutics, *J. Cereb. Blood Flow Metab.*, vol. 18, No. 1, Jan. 1998, 42 pages (pp. 2-25).
THOR: Is LLT Different from Ultrasound?, http://www.thorlaser.com/LLLT/is-LLLT-diff-from-ultrasound.htm, 2 pages, Oct. 13, 2004.
THOR, Specification, 30mW Red Laser probe, www.thorlaser.com/specs/680.html, web page (1 page), Oct. 6, 1999.
THOR Laser, 100mW, Thor, lllt, LLLT, Low Level Laser Therapy, low level laser therapy, Lazer, Thorl., http://www.thorlaser.com/specs/100m W.html, Oct. 6, 1999, p. 1.
THOR, Specification, 200mW/810nm Laser probe, http://www.thorlaser.com/specs/200mWhtml, web page (1 page), Oct. 6, 2009.
THOR, Specification, 200mW/650nm Laser probe, http://www.thorlaser.com/specs/200mW650nm.html, web page (1 page), Oct. 6, 1999.
THOR, Specification, 500mW/810nm Laser probe, http://www.thorlaser.com/specs/ 500mW.html, web page (1 page), Oct. 6, 1999.
THOR Laser, Specifications, THOR: Specifications, Thor, lllt, LLLT, Low Level Laser Therapy, low level laser therapy, http://www.thorlaser.com/specs, Oct. 6, 1999, pp. 1-2.
THOR: Product List, Thor, lllt, LLLT, Low Level Laser Therapy, Laz., http://www.thorlaser.com/prodlist/index.html, Oct. 6, 1999, pp. 1-4.
Toon, John, Taking the "Ouch" Out of Needles: Arrays of Micron-Scale "Microneedles" Offer New Technique for Drug Delivery, *Georgia Tech Research News*, Jun. 22, 1998 (three pages).
Toricelli, P., et al., Laser Biostimulation of cartilage: in vitro evaluation, *Biomed. Pharmacother.*, 2001, vol. 55, pp. 117-120.
Tuchin, Valery, Tissue Optics: Light Scattering Methods and Instruments for Medical Diagnosis, SPIE Press, Tutorial Texts in *Optical Engineering*, vol. TT38, 2000, pp. 3-11, 2000.
Tunér, Jan, et al., Low Level Laser Therapy, Clinical Practice and Scientific Background, Prima Books in Sweden AB, 1999, pp. 1-9, 45-58, 62-114, 113-116, 118, 132-134, 134-135, 149-151, 151-156, 185, 334-364.
Van Breugel, Hans H.F.I., et al., Power Density and Exposure Time of He-Ne Laser Irradiation are More Important than Total Energy Dose in Photo-Biomoducation of Human Fibroblasts InVitro, *Lasers in Surgery and Medicine* (1992), Wiley-Liss, Inc., pp. 528-537.
Van Breugel et al. "He-Ne laser irradiation affects proliferation of cultured rat-Schwann cells in a dose-dependent manner," Journal of Neurocytology 22, 185-190 (1993).
Weiss, N. et al., "Enhancement of Muscle Regeneration in the Rat Gastrocnemius Muscle by Low Energy Laser Irradiation", Anat. Embroyl. (1992), vol. 186, pp. 497-503.
Wong-Riley, Margaret T.T., et al., Light-emitting diode treatment reverse the effect of TTX on cytochrome oxidase in neurons, *NeuroReport*, vol. 12, No. 14, Oct. 8, 2001, pp. 3033-3037.
Yaakobi, Tali, et al., Long-term effect of low energy laser irradiation on infarction and reperfusion injury in the rat heart, *J. Appl. Physiol.*, vol. 90, 2001, pp. 2411-2419.
"Is Laser Therapy Overtaking Ultrasound?" http://www.laser.uk.com/laser, Therapy vs. ultrasound.html, dated Feb. 20, 1999.
"Laser Exposure Limits & Hazard Calculations," Excerpts from OSHA Technical Manual, Chapter 6: Laser Hazards, date unknown.
Accelrys, "Optical Absorption Spectra of Melanins—a Comparison of Theoretical and Experimental Results," Chemicals Case Study, Accelyrys, Oct. 5, 2005, http://accelrys.com/references/case-studies/archive/studies/melanins_partII.pdf.
Adamic, Metka et al., "Vascular lasers and IPLS: Guidelines for care from the European Society for Laser Dermatology (ESLD)," Journal of Cosmetic and Laser Therapy, 2007; 9: 113-124.
Albertini, R. et al., "COX-2 mRNA expression decreases in the subplantar muscle of rat paw subjected to carrageenan-induced inflammation after low level laser therapy," Inflammation Research, 56 (2008) pp. 228-229.
Albrecht-Buehler, Guenter. "Reversible, excitation light-induced enhancement of fluorescence of live mammalian mitochondria," The FASEB Journal, vol. 14, Oct. 2000, pp. 1864-1866.

Alerstam, Erik et al., "Parallel computing with graphics processing units for high-speed Monte Carlo simulation of photon migration," Journal of Biomedic Optics, vol. 13(6), Nov./Dec. 2008.
Amat, Albert et al., "Modification of the intrinsic fluorescence and the biochemical behavior of ATP after irradiation with visible and near-infrared laser light," Journal of Photochemistry and Photobiology B: Biology 81 (2005) 26-32.
Anders et al., Low power laser irradiation alters the rate of regeneration of the rat facial nerve, Laser Surg. Med., 13:72-82 (1993).
Anders, Juanita J., "The Potential of Light Therapy for Central Nervous System Injury and Disease," Photomedicine and Laser Surgery, vol. 27, No. 3 (2009) pp. 379-380.
Anonymous, "Engineer, heal thyself," News Brief, Optoelectronics Report 3, www.optoelectronics-world.com, Nov. 1, 1999.
Arthur, Charles R., "Parkinson's Disease Brain Mitochondria Have Impaired Respirasome Assembly, Age-Related Increases in Distribution of Oxidative Damage to mtDNA and No Differences in Heteroplasmic mtDNA Mutation Abundance," Molecular Degeneration, http://www.molecularneurodegeneration.com/content/4/1/37, Sep. 23, 2009.
Atamna, Hani et al., "Mechanisms of mitochondrial dysfunction and energy deficiency in Alzheimer's disease," Mitochondrion 7 (2007) pp. 297-310.
Ataullakhanov et al. "What Determines the Intracellular ATP Concentration," Bioscience Reports, vol. 22, No. 5 and 6, Oct. and Dec. 2002.
Avni, Dorit et al., "Protection of Skeletal Muscles from Ischemic Injury: Low-Level Laser Therapy Increases Antioxidant Activity", Photomedicine and Laser Surgery vol. 23, No. 3, 2005, p. 273-277.
Barnett, Alex H. et al., "Robust inference of baseline optical properties of the human head with three-dimensional segmentation from magnetic resonance imaging," Applied Optics, vol. 42, No. 16, Jun. 1, 2004, pp. 3095-3108.
Bashkatov, A.N. et al., "Estimate of the melanin content in human hairs by the inverse Monte-Carlo method using a system for digital image analysis," Quantum Electronics 36(12) 1111-1118 (2006).
Baxter, Richard, "Laser Safety Training Manual," University of Chicago Chemistry Department, date unknown.
Beal, M. Flint, "Mitochondrial Dysfunction and Oxidative Damage in Alzheimer's and Parkinson's Diseases and Coenzyme Q10 as a Potential Treatment," Journal of Bioenergetics and Biomembranes, vol. 26, No. 4, Aug. 2004, pp. 381-386.
Beauvoit, B. et al. "Contribution of the Mitochondrial Compartment to the Optical Properties of the Rat Liver: A Theoretical and Practical Approach," Biophysical Journal, vol. 67, Dec. 1994, pp. 2501-2510.
Ben-Shachar, Dorit et al., "Neuroanatomical Pattern of Mitochondrial Complex I Pathology Varies between Schizophrenia, Bipolar Disorder and Major Depression," PLoS One, Nov. 2008, vol. 3, Issue 11.
Bisland, Stuart K. et al., "To begin at the beginning: The science of bio-stimulation in cells and tissues," Proc. of SPIE, vol. 6140, 2006.
Boelens, R. et al., "EPR Studies of the Photodissociation Reactions of Cytochrome c Oxidase-Nitric Oxide Complexes," Biochimica et Biophysica Acta, 679 (1982) pp. 84-94.
Boelens, Rolf et al., "An EPR Study of the Photodissociation Reactions of Oxidised Cytochrome c Oxidase-Ntiric Oxide Complexes," Biochimica et Biophysica Acta, 924 (1983) pp. 176-183.
Bonnet, Sébastien et al., "A Mitochondria-K+ Channel Axis is Suppressed in Cancer and its Normalization Promotes Apoptosis and Inhibits Cancer Growth," Cancer Cell 11, 37-51, Jan. 2007.
Borutaite, Vilmante et al., "Reversal of nitric oxide-, peroxynitrite- and S-nitrosothiol-induced inhibition of mitochondrial repiration or complex I activity by light and thiols," Biochimica et Biophysica Acta, 1459, (2000) pp. 405-412.
Brain Injury Source, vol. 3, Issue 4 (1999).
Brennan, Angela M. et al., "NADPH oxidase is the primary source of superoxide induced by NMDA receptor activation," Nature Neuroscience, vol. 12, No. 7, Jul. 2009, pp. 857-864.
Brown, G.C., "Mechanisms of inflammatory neurodegeneration: iNOS and NADPH oxidase," Biochemical Society Transactions (2007) vol. 35, part 5, pp. 1119-1121.
Bruch, Reinhard. "Low Level Laser Therapy (LLLT)," Nevada Health Forum, Dec. 4, 2003.

Buckman, Jennifer F. et al., "Spontaneous Changes in Mitochondrial Membrane Potential in Cultured Neurons," The Journal of Neuroscience, Jul. 15, 2001, 21(14): 5054-5065.

Bullock, M. Ross et al., "Outcome measures for clinical trials in neurotrauma," Neurosurg. Focus 13 (1): Jul. 2002, pp. 1-11.

Calabrese, Vittorio et al., "Nitric oxide in the central nervous system: neuroprotection versus neurotoxicity," Nature Reviews: Neuroscience, vol. 8, Oct. 2007, pp. 766-775.

Carroll, James D., "A 3D dose model for low level laser/led therapy biostimulation and bioinhibition," Proc. of SPIE, vol. 6846, 2008.

Carroll, James S et al., "Red Blood Cell Stimulation of Platelet Nitric Oxide Production Indicated by Quantitative Monitoring of the Communication between Cells in the Bloodstream," Analytical Chemistry, vol. 79, No. 14, pp. 5133-5138, Jul. 15, 2007.

Castello, Pablo et al., "Oxygen-regulated isoforms of cytochrome c oxidase have differential effects on its nitric oxide production and on hypoxic signaling," PNAS Early Edition, www.pnas.org/cgi/doi/10.1073/pnas.0709461105, 2008.

Catanzaro et al. "Managing Tissue Heating in Laser Therapy to Enable Double-Blind Clinical Study," Proc. SPIE, vol. 6140, 614000 (2006).

Cellular Model Studies of Brain-Mediated Monochromatic Phototherapy on Alzheimer's Disease, Chinese Journal of Lasers, 0258-7-25 (2009) Supplement 1-0190-04.

Celsi, Fulvio et al., "Mitochondria, calcium and cell death: A deadly triad in neurodegeneration," Biochim. Biophys. Acta., May 2009; 1787(5): 335-344.

Chan, C. Savio et al., "Rejuvenation protects neurons in mouse models of Parkinson's disease," Nature, vol. 447, Jun. 28, 2007.

Chance, Britton, "The stopped-flow method and chemical intermediates in enzyme reactions—a personal essay," Personal perspective, Photosynthesis Research 2004, p. 387-400.

Chen, Aaron Chih-Hao et al., "Low Level Laser Therapy activates NF-kB via Generation of Reactive Oxygen Species in Mouse Embryonic Fibroblasts," Proc. of SPIE, vol. 7165, 2009.

Chen, James et al., "New Technology for Deep Light Distribution in Tissue for Phototherapy," The Cancer Journal, vol. 8, No. 2, Mar./Apr. 2002, pp. 154-163.

Choi, JeeHyun et al, "Noninvasive determination of the optical properties of adult brain: near-infrared spectroscopy approach," Journal of Biomedical Optics 9(1), pp. 221-229 (Jan./Feb. 2004).

Chow, Roberta T. et al., "830nm laser irradiation induces varicosity formation, reduces mitochondrial membrane potential and blocks fast axonal flow in small and medium diameter rat dorsal root ganglion neurons: implications for the analgesic effect of 830nm laser," Journal of the Peripheral Nervous System, 12:28-39 (2007).

Custo, Anna et al., "Comparison of Diffusion and Transport in human head," date unknown.

Custo, Anna et al., "Effective scattering coefficient of the cerebral spinal fluid in adult head models for diffuse optical imaging," Applied Optics, vol. 45, No. 19, Jul. 1, 2006, pp. 4747-4756.

Dawson, Elizabeth et al., "Adverse Events Associated With Nonablative Cutaneous Laser, Radiofrequency, and Light-Based Devices," Seminars in Cutaneous Medicine and Surgery, 2007, pp. 15-21.

de Groot, A.C. et al., "Bijwerkingen van Lasertherapie," Nederlands Tijdschrift voor Dermatologie & Venereologie, vol. 16, Sep. 2006 (in Dutch).

Delori, François et al., "Maximum permissible exposures for ocular safety (ANSI 2000), with emphasis on ophthalmic devices," J. Opt. Soc. Am. A., vol. 24, No. 5, May 2007, pp. 1250-1265.

Demaurex, Nicolas et al., "Reactive oxygen species are NOXious for neurons," Nature Neuroscience, vol. 12, No. 7, Jul. 2009, pp. 819-820.

Desmet, et al.: "Clinical and Experimental Applications of NIR-LED Photobiomodulation"—Photomedicine and Laser Surgery—2006;24(2): 121-128.

DeTaboada, L., et al.: "Transcranial Application of Low-Energy Laser Irradiation Improves Neurological Deficits in Rats Following Acute Stroke", Lasers in Surgery and Medicine 38:70-73 (2006).

Dhar, Shilpa S. et al., "Chromosome Conformation Capture of all 13 Genomic Loci in the Transcriptional Regulation of the Multi-subunit Bigenomic Cytochrome C Oxidase in Neurons," The Journal of Biological Chemistry. 2009.

Encyclopaedia Britanica Article—"electromagnetic field" Encyclopaedia Brittanica Online, accessed Feb. 17, 2006.

EPO Extended Search Report re Appl. No. 10182415.9, dated Nov. 26, 2010.

Franceschini, Maria Angela et al., "Near-Infrared Absorption and Scattering Spectra of Tissues in Vivo," 1999.

Frigo, Lucio et al., "The effect of low-level laser irradiation (Ga-Al-AsP—660nm) on in vitro and in vivo melanoma," http://www.biomedcentral.com/1471-2407/9/404, Nov. 20, 2009.

Galuzzi, Lorenzo et al., "Targeting post-mitochondrial effectors of apoptosis for neuroprotection," Biochim. Biophys. Acta (2008), doi:10.1016/j.bbabio.2008.09.006.

Gao, Zuejuan et al., "Molecular mechanisms of cell proliferation induced by low power laser irradiation," Journal of Biomedical Science, 16:4, 2009.

Gasparyan, Levon et al., "Activation of Angiogenesis Under Influence of Red Low Level Laser Radiation," Laser Florence, 2004, pp. 1-8.

Giuliani, Alessandro et al., "Low infra red laser light irradiation on cultured neural cells: effects on mitochondria and cell viability after oxidative stress," BMC Complementary and Alternative Medicine 2009, 9:8.

Goldstein, Larry B. et al., "Patient Safety in Trials of Therapy for Acute Ischemic Stroke," The Journal of the American Medical Association, vol. 287, No. 8, Feb. 27, 2002.

Gourley, Paul L. et al., "Optical Phenotyping of Human Mitochondria in a Biocavity Laser," IEEE Journal of Selected Topics in Quantum Electronics, vol. 11, No. 4, Jul./Aug. 2005.

Haitsma, Iain K. et al., "Monitoring cerebral oxygenation in traumatic brain injury," Progress in Brain Research, vol. 161, Chapter 14, pp. 207-216, 2007.

Hamblin et al. "Mechanisms of Low Level Light Therapy," Proc. of SPIE, vol. 6140 614001-1 (2006).

Han May H. et al., "Proteomic analysis of active multiple sclerosis lesions reveals therapeutic targets," Nature vol. 451, Feb. 2008, p. 1076-1081.

Hancock, Celeste M. et al., "Modulation of Pain in Osteoarthritis: The Role of Nitric Oxide," Clin. J. Pain, vol. 24, No. 4, May 2008, pp. 353-365.

Harris, David M et al., "Laser Biostimulation: Review and Hypothesis," Laser Topics, 1988, pp. 9-14.

Häusser, Michael et al., "Controlling neural circuits with light," Nature: News & Views, vol. 446, Apr. 5, 2007, pp. 617-619.

Hawkins, Denise et al., "How Long After Laser Irradiation Should Cellular Responses be Measured to Determine the Laser Effects?" Journal of Laser Applications, vol. 19, No. 2, May 2007, pp. 74-83.

Hawkins-Evans, Denise et al., "Effect of Wavelength and Fluence on Morphology, Cellular and Genetic Integrity of Diabetic Wounded Human Skin Fibroblasts," Proc. of SPIE vol. 6140, p. 614006-1 to 614006-13 (2006).

Hawkins-Evans, Denise et al., "Efficacy of a single high does versus multiple low doses of LLLT on wounded skin fibroblasts," Proc. of SPIE vol. 6632, p. 66321U-1 to 66321U-12 (2007).

Henchcliffe, Claire et al., "Mitochondrial biology and oxidative stress in Parkinson disease pathogenesis," Nature Clinical Practice Neurology, vol. 4, No. 11, Nov. 2008.

Hilf, Russell, "Mitochondria are targets of photodynamic therapy," J. Bioenerg. Biomembr. (2007) 39:85-89.

Hollenbeck, Peter J., "The Pattern and Mechanism of Mitochondrial Transport in Axons," Frontiers in Bioscience 1, Jul. 1, 1996.

Hori, Yasuaki et al., "Automatic characterization and segmentation of human skin using three-dimensional optical coherence tomography," Optics Express, vol. 14, No. 5, Mar. 6, 2006, pp. 1862-1877.

Hu, Wan-Ping et al., "Helium-Neon Laser Irradiation Stimulates Cell Proliferation through Photostimulatory Effects in Mitochondria," Journal of Investigative Dermatology (2007), vol. 127, pp. 2048-2057.

Hüttemann, Maik et al., "Regulation of oxidative phosphorylation, the mitochondrial membrane potential, and their role in human disease," J. Bioenerg. Biomembr (2008) 40:445-456, pp. 445-456.

Ilic, S., et al.: "Effects of Power Densities, Continuous and Pulse Frequencies, and Number of Sessions of Low-Level Laser Therapy on Intact Rat Brain" Photomedicine and Laser Surgery—2006; 24(4): 458-466.

International Examination Report for EP 04 783 805, dated Jan. 19, 2010.

Izzetoglu, Meltem et al., "Functional Brain Imaging Using Near-Infrared Technology, Assessing Cognitive Activity in Real-Life Situations" IEEE Engineering in Medicine and Biology Magazine, Jul./Aug. 2007, p. 38-46.

Jacques, Steven L. "Skin Optics," Oregon Medical Laser Center News, Jan. 1998, http://omlc.ogi/edu/news/jan98/skinoptics.html.

Jacques, Steven L. et al., "Tutorial on diffuse light transport," Journal of Biomedical Optics, 13(4), 041302 (Jul./Aug. 2008).

Jekabsone, Aiste et al., "Nitric oxide from neuronal nitric oxide synthase sensitises neurons to hypoxia-induced death via competitive inhibition of cytochrome oxidase," Journal of Neurochemistry, 2007.

Jou, Shaw-Hwa et al., "Mitochondrial Dysfunction and Psychiatric Disorders," Chang Gung Med. J., vol. 32, No. 4, Jul.-Aug. 2009, pp. 370-379.

Kahn, Fred et al., "Low Intensity Laser Therapy: The clinical approach," Proc. of SPIE, vol. 6140, 2008.

Karu et al. "Cell Attachment to Extracellular Matrices is Modulated by Pulsed Radiation at 820 nm and Chemicals that Modify the Activity of Enzymes in the Plasma Membrane," Lasers in Surgery and Medicine, 29: 274-281 (2001).

Karu, T.I., "Cellular mechanisms of low-power laser therapy," Proc. of SPIE, vol. 5149, 2003, pp. 60-66.

Karu, Tiina I, "Mitochondrial Signaling in Mammalian Cells Activated by Red and Near-IR Radiation," Photochemistry and Photobiology, 2008, 84: 1091-1099.

Karu, Tiina I. et al., "A Novel Mitochondrial Signaling Pathway Activated by Visible-to-near Infrared Radiation," Photochemistry and Photobiology, 2004, 80: 366-372.

Karu, Tiina I. et al., "Cellular Effects of Low Power Laser Therapy Can be Mediated by Nitric Oxide," Lasers in Surgery and Medicine, 36:307-314 (2005).

Karu, Tiina I. et al., "Changes in absorbance of monolayer of living cells induced by laser irradiation at 633, 670, and 820 nm," Proc. of SPIE, vol. 4431, 2002, pp. 306-312.

Karu, Tiina I. et al., "Irradiation with a diode at 820 nm induces changes in circular dichroism spectra (250-780 nm) of living cells," Proc. of SPIE, vol. 4433, 2001, pp. 97-102.

Karu, Tiina, "Primary and secondary mechanisms of action of visible to near-IR radiation on cells," Journal of Photochemistry and Photobiology, 49 (1999) pp. 1-17.

Karu, Tiina, "Primary mechanisms of action of low-intensity laser light on cells," SPIE, vol. 3829, 1999, pp. 42-53.

Karu, Tiina. "Can a mechanism based on changes in redox properties of cytochrome c oxidase be crucial in explaining of low-power laser effects?" SPIE, vol. 3732, 1999. pp. 202-213.

Khodjakov, Alexey et al., "Laser micro-irradiation of mitochondria: is there an amplified mitochondrial death signal in neural cells?" Mitochondrion 3 (2004) pp. 217-227.

Kiguchi, Masashi et al., "Comparison of light intensity on the brain surface due to laser exposure during optical topography and solar irradiation," Journal of Biomedical Optics 12(6), Nov./Dec. 2007.

Kim, Kyunghan et al., "Ultrafast Laser Radiation and Conduction Heat Transfer in Biological Tissues," Proceedings of IMECE2005, 2005 ASME International Mechanical Engineering Congress and Exposition, Nov. 5-11, 2005.

Kofke, W. Andrew et al., "Near Infrared Laser Therapy," University of Pennsylvania, 2009.

Lampl, Yair, "Laser treatment for stroke," Expert Rev. Neurotherapeutics 7(8), 2007.

Lane, Nick "Power Games" Nature/vol. 443/26 Oct. 2006, Nature Publishing Group, pp. 901-903.

Lapchak, Paul A. "Transcranial Near-Infrared Laser Therapy Improves Behavior and Differentially Regulates the Expression of Rapid Response Elements (Genes) in Rabbits Following Embolic Strokes," Stroke 2009; 40; e214; Abstracts From the 2009 International Stroke Conference.

Lapchak, Paul A. et al., "Advances in ischemic stroke treatment: neuroprotective and combination therapies," Expert Opin. Emerging Drugs, Mar. 2007, vol. 12, No. 1, pp. 97-112.

Lapchak, Paul A. et al., "Safety Profile of Transcranial Near-Infrared Laser Therapy Administered in Combination with Thrombolytic Therapy to Embolized Rabbits," Stroke, Nov. 2008.

Li, Ming-jun, "Managing nonlinearity in optical fiber for high-power lasers," The International Society for Optical Engineering, SPIE Newsroom, 2006.

Liang, et al.,: "Photobimodulation Partially Rescues Visual Cortical Neurons from Cyanide-Induced Apoptosis"—Neuroscience 2006;139: 639-649.

Liang, H.L. et al., "Near-Infrared Light Via Light-Emitting Diode Treatment is Therapeutic Against Rotenone- and 1-Methyl-4-Phenylpyridinium Ion-Induced Neurotoxicity," Neuroscience 153 (2008) 936-974.

Liesz, Arthur et al., "Regulatory T cells are key cerebroprotective immunomodulators in acute experimental stroke," Nature Medicine, Jan. 25, 2009.

Lievens, P.O, "The Effect of I.R. Laser Irradiation on the Vasomotricity of the Lymphatic System," Lasers in Medical Science, vol. 5:189, 1991.

Lisman et al. "Two Light-Induced Processes in the Photoreceptor Cells of Limulus Ventral Eyes," The Journal of General Physiology, vol. 58, pp. 544-561, 1971.

Liu, Timon Cheng-Yi et al., "Cellular rehabilitation of photobiomodulation," Proc. of SPIE, vol. 6534, 2007.

Lohr, Nicole L. et al., "Enhancement of nitric oxide release from nitrosyl hemoglobin and nitrosyl myoglobin by red/near infrared radiation: Potential role in cardioprotection," Journal of Molecular and Cellular Cardiology 47 (2009) 256-263.

Longo, Leonardo et al., "Amyotrophinc Lateral Sclerosis (ALS) treated with Low Level LASER Therapy (LLLT): a case report," Laser Florence 2008, A Bridge to the Laser Mediciane World, p. 96-98.

Lopes-Martins, Rodrigo Alvaro Brandão et al, "Steroids block the anti-inflammatory effects of low level laser therapy," Proc. of SPIE, vol. 6140, 2006.

Lubart, Rachel et al., "Broadband Visible Light Induced NO Formation," 2009, http://proceedings.aip.org/proceedings/cpcr.jsp.

Lubart, Rachel et al., "Low-Energy Laser Irradiation Promotes Cellular Redox Activity," Photomedicine and Laser Surgery, vol. 23, No. 1, 2005, pp. 3-9.

Luo, Gang-Yue et al, "Membranotropic photobiomodulation on red blood cell deformability," Proc. of SPIE, vol. 6534, 2007.

Lychagov, V. V., et al.: "Experimental study of cadavers head transmittance", Saratov Fall Meeting 2004: Optical Technologies in Biophysics and Medicine VI, Proc. of SPIE vol. 5771, pp. 328-331.

Macklis, Jeffrey D., "Transplanted Neocrotical Neurons Migrate Selectively into Regions of Neuronal Degeneration Produced by Chromophore-targeted Laser Photolysis," The Journal of Neuroscience, Sep. 1993, 13(9); 3848-3863.

Maegawa, Yasuyo et al., "Effects of Near-Infrared Low-Level Laser Irradiation on Microcirculation," Lasers in Surgery and Medicine, 27:427-437 (2000).

Manczak, Maria et al., "Mitochondria are a direct site of Aβ accumulation in Alzheimer's disease neurons: implications for free radical generation and oxidative damage in disease progression," Human Molecular Genetics, 2006, vol. 15, No. 9, pp. 1437-1449.

Marshall, Laura S., "Hope after failure in clinical trials," BusinessScan, BioPhotonics, Apr. 2009.

Martin, Joan B., "Light Activated Tissue Regeneration and Therapy," Notes, Aug. 2004.

Mason, Maria G. et al., "Nitric oxide inhibition of respiration involves both competitive (heme) and noncompetitive (copper) binding to cytochrome c oxidase," PNAS, vol. 103, pp. 708-713, Jan. 9, 2006.

Matas et al. "Eliminating the Issue of Skin Color in Assessment of the Blanch Response," Advances in Skin & Wound Care, vol. 14 (4, Part 1 of 2), pp. 180-188, Jul./Aug. 2001.

McClelland, Robyn L. et al., "Neurologic Correlates of Infarction-Like Lesion Location on Magnetic Resonance Imaging in the Cardiovascular Health Study," Journal of Stroke and Cerebrovascular Disease, vol. 9, No. 5, Sep.-Oct. 2000; pp. 218-228.

McKinlay, A.F. et al., "Biological Bases of Maximum Permissible Exposure Levels of Laser Standards," J. Soc. Radiol. Prol. 4 (1), 1984.

Meguro, Toshinari et al., "Caspase Inhibitors Attenuate Oxyhemoglobin-Induced Apoptosis in Endothelial Cells," Stroke, 2001; 32; 561-566.

Mester, Endre et al., "The Biomedical Effects of Laser Application," Lasers in Surgery and Medicine, 5:31-39 (1985).

Mirsky, N. et al., "Promotion of Angiogenesis by Low Energy Laser Irradiation," Antioxidants & Redox Signaling, vol. 4, No. 5, 2002, pp. 785-791.

Mochizuki-Oda, Noriko et al., "Effects of Near-Infrared Laser on Neural Cell Activity," American Institute of Physics, 2004, pp. 192-195.

Mohanty, Samarendra Kumar et al., "Generation of ROS in cells on exposure to CW and pulsed near-infrared laser tweezers," Photochemical & Photobiological Sciences, 2006, pp. 134-139.

Molinaro, M., "Light/Tissue Interaction IST 8A," Lecture #5, Jan. 23, 2006.

Moncada, Salvador et al., "Nitric oxide, cell bioenergetics and neurodegeneration," Journal of Neurochemistry, 2006, 97, pp. 1676-1689.

Moriyama, Yumi et al., "In Vivo Study of the Inflammatory Modulating Effects of Low-level Laser Therapy on iNOS Expression Using Bioluminescence Imaging," Photochemistry and Photobiology, 2005, 81: 1351-1355.

Moser, Christopher C. et al., "Darwin at the molecular scale: selection and variance in electron tunneling proteins including cytochrome c oxidase," Philosophical Transactions of the Royal Society B, 2006, 361: 1295-1305.

Mthunzi, Patience et al., "Influence of Beam Shape on in-vitro Cellular Transformations in Human Skin Fibroblasts," Proc. of SPIE, vol. 5876, 2005.

Mudra, R. et al., "Analysis of near-infrared spectroscopy and indocyanine green dye dilution with Monte Carlo simulation of light propagation in the adult brain," Journal of Biomedical Optics, 11(4), Jul./Aug. 2006.

Myers, D.R. et al., "Proposed Reference Spectral Irradiance Standards to Improve Concentrating Photovoltaic System Design and Performance Evaluation," National Renewable Energy Laboratory, May 2002.

Naviaux, Robert K., "Mitochondria-Light Interactions—Mechanisms of Cell Sparing and Regeneration," The Mitochondrial and Metabolic Disease Center, 2007.

Ng, Kwan-Hoong, "Non-Ionizing Radiations—Sources, Biological Effects, Emissions and Exposures," Proceedings of the International Conference on Non-Ionizing Radiation at UNITEN, Electromagnetic Fields and Our Health, Oct. 10-22, 2003.

Nilsson, Thomas, "Photoinduced electron transfer from tris(2,2'-bipyridyl)ruthenium to cytochrome c oxidase," Proc. Natl. Acad. Sci. USA 89 (1992) pp. 6497-6501.

Okada, Eiji et al, "Near-infrared light propagation in an adult head model. II. Effect of superficial tissue thickness on the sensitivity of the near-infrared spectroscopy signal," Applied Optics, Jun. 1, 2003, vol. 42, No. 16, pp. 2915-2922.

Optical Properties of Tissue with Strong (Multiple) Scattering, source unknown.

Oron, Uri et al.: Low-Level Laser Therapy Applied Transcranially to Rats After Induction of Stroke Significantly Reduces Long-Term Neurological Deficits, Stroke, 2006; 37:2620-2624.

Osipov, A.N. et al., "Biological Activity of Hemoprotein Nitrosyl Complexes," Biochemistry, 2007, vol. 72, No. 13, pp. 1491-1504.

Palacios-Callender, Miriam et al., "Cytochrome c-oxidase regulates endogenous nitric oxide availability in respiring cells: A possible explanation for hypoxic vasodilation," PNAS, Nov. 20, 2007, vol. 104, No. 47, pp. 18508-18513.

Parathath, Susana R. et al., "Nitric Oxide Synthase Isoforms Undertake Unique Roles During Excitotoxicity," Stroke 2007; 38; 1938-1945.

Parihar, Mordhwaj S., "Mitoenergetic failure in Alzheimer disease," Am J Physiol Cell Physiol, 292:8-23, 2007.

Passarella, S., et al.: "Increase in the ADP/ATP Exchange in Rat Liver Mitochondria Irradiated In Vitro by Helium-Neon Laser", Biochemical and BioPhysical Research Communications, vol. 156, No. 2, Oct. 31, 1988, pp. 978-986.

Peterson, Jill et al., "Material Properties of the Human Cranial Vault and Zygoma," The Anatomical Record Part A, 274A:785-797 (2003).

Pislea, Mihaela et al., "Low Level Long Wavelength Laser Irradiation Effects on Cells Cycle Progression and Apoptosis of Energy Restricted Jurkat T-Cells," Romanian J. Biophys., vol. 19, No. 1, pp. 1-18, 2009.

Pogue, BW et al., "Transient absorption changes in vivo during photodynamic therapy with pulsed-laser light," British Journal of Cancer (1999) 80(3/4), pp. 344-351.

Popp, Fritz-Albert, "On the Coherence of Ultraweak Photon Emission from Living Tissues," Disequilibrium and Self-Organisation, pp. 207-230, 1986.

Powers, William J. et al., "Cerebral mitochondrial metabolism in early Parkinson's disease," Journal of Cerebral Blood Flow & Metabolism (2008) 28, 1754-1760.

Ratner, Mark L., "The Alzheimer's Divide," In Vivo, Sep. 2008.

Respond Systems, Inc., "Understanding Low Level Laser Therapy," 1991.

Reznikov, L.L. et al., "The Biomechanism of Low-Energy Laser Irradiation is Similar to General Adaptive Reaction," Proc. SPIE, vol. 2086, 380 (1994).

Rochkind, S. et al., "New trend in neuroscience: Low-power laser effect on peripheral and central nervous system (basic science, preclinical and clinical studies)," Neurological Research, vol. 14, Mar. 1992, pp. 2-11.

Rohn, Troy T. et al., "Caspases as Therapeutic Targets in Alzheimer's Disease: Is it Time to 'Cut' to the Chase?" Int J Clin Exp Pathol (2009) 2, pp. 108-118.

Rose, Andreas et al., "Mode Field Pertubations and Numerical Aperture Broadening Due to Angular Misalignment in Multimode Fiber Coupling," Proc. of SPIE, vol. 7173, 2009.

Roynesdal, A.K. et al., "The effect of soft-laser application on postoperative pain and swelling, A double-blind, crossover study," International Journal of Oral Maxillofacial Surgery, 1993: 22: 242-245.

Sarasa, Manuel et al., "Natural Non-Transgenic Animal Models for Research in Alzheimer's Disease," Current Alzheimer's Research, 2009, 6, pp. 171-178.

Savchenko, Eugeny P., et al.: "Monte-Carlo simulation of brain activity response for intense NIR-radiation", Proc. of SPIE vol. 5696, Mar. 29, 2005, pp. 232-239.

Schaffer, Chris B. et al., "Two-Photon Imaging of Cortical Surface Microvessels Reveals a Robust Redistribution in Blood Flow after Vascular Occlusion," PLOS Biology, Feb. 2006, vol. 4, Issue 2, pp. 0258-0270.

Scheele, Jürgen S. et al., "Kinetics of NO Ligation with Nitric-oxide Synthase by Flash Photolysis and Stopped-flow Spectrophotometry," The Journal of Biological Chemistry, vol. 274, No. 19, May 1999, pp. 13105-13110.

Schumm N., "Multiple Sclerosis, Laser Blood Irradiation, Quality of Life" SF12, Komplement. Intergr. Med. Nov./Dec. 2008.

Seremet, Teofila et al., "Photobiomodulation of Quercetin Antiproliferative Effects Seen in Human Acute Leukemia Jurkat Cells," Romanian J. Biophys., vol. 17, No. 1, pp. 33-43, 2007.

Sharpe, Martyn A., "Interaction of Peroxynitrite with Mitochondrial Cytochrome Oxidase," The Journal of Biological Chemistry, vol. 273, No. 47, Nov. 20, 1998, pp. 30961-30972.

Shichita, Takashi et al., "Pivotal role of cerebral interleukin-17-producing γδT cells in the delayed phase of ischemic brain injury," Nature Medicine, vol. 15, No. 8, Aug. 2009, pp. 946-951.

Shimada, Sachihiro et al., "Intracellular disruption of mitochondria in a living HeLa cell with 76-MHz femtosecond laser oscillator," Optics Express, vol. 13, No. 24, Nov. 28, 2005, pp. 9869-9880.

Shiva, Struti, "Shining a light on tissue NO stores: Near infrared release of NO from nitrite and nitrosylated hemes," Journal of Molecular and Cellular Cardiology, 46, 2009, pp. 1-3.

Sieron, A. et al., "Our Own Experience in Clinical Use of Low Power Laser Therapy," Przegl Lek, 1995; 52(1):13-5.

Siposan, Dan G. et al., "Effect of Low-Level Laser Radiation on Some Rheological Factors in Human Blood: An in Vitro Study," Journal of Clinical Laser Medicine & Surgery, vol. 18, No. 4, 2000, pp. 185-195.

Smith, Rich, "Seeing the Light: How light therapy is surprising skeptics and gaining converts," Physical Therapy Products, Apr./May 2004.

Snyder, S.K., et al., "Quantitation of calcitonin gene-related peptide mRNA and neuronal cell death in facial motor nuclei following axotomy and 633 nm low power laser treatment," Surg. Med., 31:216-222 (2002).

Soane, Lucian et al., "Mechanisms of Impaired Mitochondrial Energy Metabolism in Acute and Chronic Neurodegenerative Disorders," J. Neurosci. Res., Nov. 15, 2007; 85(15): 3407-3415.

Sommer, A, et al., "Biostimulatory Windows in Low-Intensity Laser Activation: Lasers, Scanners, and NASA's Light-Emitting Diode Array System," Journal of Clinical Laser Medicine & Surgery, vol. 19, No. 1, 2001, pp. 29-33.

Stoll, Christian et al., "Quantum Dots on Gold: Electrodes for Photoswitchable Cytochrome c Electrochemistry," Small Journal, 2006, vol. 2, No. 6, pp. 741-743.

Stopp, Sebastian et al., "A new concept for navigated laser surgery," Laser Med. Sci. (2008) 23:261-266.

Sukstanskii, A.L. et al., "An analytical model of temperature regulation in human head," Journal of Thermal Biology, 29 (2004), pp. 583-587.

Szundi, Istvan et al., "Flash-Photolysis of Fully Reduced and Mixed-Valence CO-Bound Rhodobacter sphaeroides Cytochrome c Oxidase: Heme Spectral Shifts," Biochemistry, 2007, 46, 12567-12578.

Tafur, Joseph et al., "Low-Intensity Light Therapy: Exploring the Role of Redox Mechanisms," Photomedicine and Laser Surgery, vol. 26, No. 4, 2008.

Tajima, H. et al., "A light-emitting diode fabricated from horse-heart cytochrome c," Solid State Communications, 126 (2003) 579-581.

Theralase Inc., "Low Level Light Therapy (LLLT)," 1999.

Therapeutic Laser Corporation, "Healing Light Healing the World," website unknown, Accessed Jul. 1, 1999.

Trimmer, Patricia A. et al., "Mitochondrial abnormalities in cybrid cell models of sporadic Alzheimer's disease worsen with passage in culture," Neurobiology of Disease, vol. 15, 2004, pp. 29-39.

Trimmer, Patricia A. et al., "Parkinson's disease transgenic mitochondrial cybrids generate Lewy inclusion bodies," Journal of Neurochemistry, (2004) 88, pp. 800-812.

Trimmer, Patricia A. et al., "Reduced axonal transport in Parkinson's disease cybrid neurites is restored by light therapy," Molecular Neurodegeneration 2009, 4:26.

Trimmer, Patricia A., "Abnormal Mitochondrial Morphology in Sporadic Parkinson's and Alzheimer's Disease Cybrid Cell Lines," Experimental Neurology, 162, 37-50 (2000).

Troy, Tamara L. et al., "Optical Properties of Human Skin in the NIR Wavelength Range of 1000-2200nm," Instrumental Metrics, Inc. (2001).

Tunér, Jan et al., "It's All in the Parameters: A Critical Analysis of Some Well-Known Negative Studies on Low-Level Laser Therapy," Journal of Clinical Laser Medicine & Surgery, vol. 16, No. 5, 1998, pp. 245-248.

Vakoc, Benjamin J. et al., "Real-time microscopic visualization of tissue response to laser thermal therapy," Journal of Biomedical Optics, Mar./Apr. 2007, vol. 12(2).

Verkruysse, Wim et al., "Infrared Measurement of Human Skin Temperature to Predict the Individual Maximum Safe Radiant Exposure (IMSRE)," Lasers in Surgery and Medicine, 39:757-766, 2007.

Villringer, Arno et al., "Non-invasive optical spectroscopy and imaging of human brain function," TINS vol. 20, No. 10, 1997.

Vladimirov, Yu. A. et al., "Molecular and Cellular Mechanisms Triggered by Low-level Laser Irradiation," Biophysics, vol. 49, No. 2, 2004, pp. 325-336.

Vladimirov, Yu. A. et al., "Photobiological Principles of Therapeutic Applications of Laser Radiation," Biochemistry (Moscow), vol. 69, No. 1, 2004, pp. 81-90.

Wang, Xinglong et al., "The Role of Abnormal Mitochondrial Dynamics in the Pathogenesis of Alzheimer's Disease," J Neurochem, May 2009, 109 (Suppl 1): 153-159.

Waynant, R., et al., "Review of Laser Therapy: Current Status and Consensus for Research Needed for Further Progress," NAALT Conference 2003.

Wells, Jonathan et al., "Biophysical Mechanisms of Transient Optical Stimulation of Peripheral Nerve," Biophysical Journal, vol. 93, Oct. 2007, pp. 2567-2580.

Willis, Gregory L., "Intraocular microinjections repair experimental Parkinsons' disease," Brain Research 1217 (2008) 119-131.

Wong-Riley, et al.: "Photobiomodulation Directly Benefits Primary Neurons Functionally Inactivated by Toxins", The Journal of Biological Chemistry—2005;280(6): 4761-4771.

Yang, Fu-Shou, "Medical Applications of Low Power Lasers in China," Laser Systems for Photobiology and Photomedicine, 1991, pp. 115-127.

Yaroslavsky, A. N. et al., "Optical properties of selected native and coagulated human brain tissues in vitro in the visible and near infrared spectral range," Physics in Medicine and Biology, 47 (2002), pp. 2059-2073.

Yi, Muqing et al., "Control of mitochondrial motility and distribution by the calcium: a homeostatic circuit," The Journal of Cell Biology, vol. 167, Nov. 22, 2004, pp. 661-672.

Young, A.E.R. et al., "Behaviour of near-infrared light in the adult human head: implications for clinical near-infrared spectroscopy," British Journal of Anaesthesia, 84 (1): 38-42 (2000).

Yu, Wei et al., "The Effect of Laser Irradiation on the Release of bFGF From 3T3 Fibroblasts," Photochemistry and Photobiology, vol. 59, No. 2, pp. 167-170, 1994.

Yujung, Kang et al., "Development of the fully automated program system; Can calculate transporting light intensity to the specific position in the brain tissue," http://pbil.kaist.ac.kr/lectures/bis500/report/proposal/team3_proposal_final.doc, accessed Apr. 30, 2007.

Zeischegg, Peter M., "Low Level Laser Therapy (LLLT)," http://www.drz.org/laser.htm, Accessed Oct. 1, 1999.

Zhang, Rong et al., "Near infrared light protects cardiomyocytes from hypoxia and reoxygenation injury by a nitric oxide dependent mechanism," Journal of Molecular and Cellular Cardiology, 46 (2009) pp. 4-14.

LOW LEVEL LIGHT THERAPY FOR ENHANCEMENT OF NEUROLOGIC FUNCTION

RELATED APPLICATION DATA

This application is a continuation of U.S. patent application Ser. No. 10/764,986, filed Jan. 26, 2004, now issued as U.S. Pat. No. 7,534,255, and incorporated in its entirety by reference herein, and which claims priority under 35 U.S.C. §119(e) to U.S. Provisional Patent Appl. Nos. 60/442,693, filed Jan. 24, 2003 and incorporated in its entirety by reference herein, 60/487,979, filed Jul. 17, 2003 and incorporated in its entirety by reference herein, and 60/537,190, filed Jan. 19, 2004 and incorporated in its entirety by reference herein.

FIELD OF THE INVENTION

The present invention relates to methods for enhancing neurologic function such as may be desired in individuals having a loss of such function, including motor function and cognitive function, including that resulting from Alzheimer's disease, dementia, heat stroke, head trauma, depression, stroke, and neurodegeneration, as well as in healthy individuals, using light therapy.

BACKGROUND OF THE INVENTION

Dementia is characterized as the loss of cognitive function having a severity so as to interfere with a person's daily activities. Cognitive function includes activities such as knowing, thinking, learning, memory, perception, and judging. Symptoms of dementia can also include changes in personality, mood, and behavior of the subject.

Dementia is a collection of symptoms that can be caused by any of a variety of diseases or conditions; it is not itself a disease. Although, in some cases, dementia can be cured by curing the underlying disease (e.g. infection, nutritional deficiency, tumor), in most cases dementia is considered incurable.

Dementia is considered a late-life disease because it tends to develop mostly in elderly people. About 5-8% of all people over the age of 65 have some form of dementia, and this number doubles every five years above that age. It is estimated that as many as half of people in their 80s suffer from some form of dementia. The most common cause of dementia is Alzheimer's disease, which affects about 4 million Americans and appears to be increasing in frequency more than most other types of dementia. Other causes of dementia include AIDS or HIV infection, Creutzfeldt-Jakob disease, head trauma (including single-event trauma and long term trauma such as multiple concussions or other traumas which may result from athletic injury), Lewy body disease, Pick's disease, Parkinson's disease, Huntington's disease, drug or alcohol abuse, brain tumors, hydrocephalus, and kidney or liver disease.

Furthermore, people suffering from mental diseases or disorders can suffer from varying levels of diminishment of cognitive function that do not rise to the level of dementia. Additionally, generally healthy individuals may also perceive some loss of cognitive function, most commonly a reduction in the function of memory. Loss or diminishment of memory may occur in any of the four commonly designated phases of memory, namely learning, retention, recall and recognition, and may be related to immediate memory, recent memory or remote memory. Loss of motor function may occur as a result of any of a number of causes, including many of those discussed above for which there is also a loss of cognitive function.

High energy laser radiation is now well accepted as a surgical tool for cutting, cauterizing, and ablating biological tissue. High energy lasers are now routinely used for vaporizing superficial skin lesions and, to make deep cuts. For a laser to be suitable for use as a surgical laser, it must provide laser energy at a power sufficient to heart tissue to temperatures over 50° C. Power outputs for surgical lasers vary from 1-5 W for vaporizing superficial tissue, to about 100 W for deep cutting.

In contrast, low level laser therapy involves therapeutic administration of laser energy to a patient at vastly lower power outputs than those used in high energy laser applications, resulting in desirable biostimulatory effects while leaving tissue undamaged. For example, in rat models of myocardial infarction and ischemia-reperfusion injury, low energy laser irradiation reduces infarct size and left ventricular dilation, and enhances angiogenesis in the myocardium. (Yaakobi et al., *J. Appl. Physiol.* 90, 2411-19 (2001)). Low level laser therapy has been described for treating pain, including headache and muscle pain, and inflammation.

SUMMARY OF THE INVENTION

The low level light therapy methods for enhancing neurologic function are based in part on the new and surprising discovery that power density (i.e., power per unit area) of the light energy applied to tissue appears to be a very important factor in determining the relative efficacy of low level light therapy, and particularly with respect to enhancing the function of neurons in both healthy and diseased states.

In accordance with one embodiment there are provided methods directed toward the enhancement of neurologic function in a subject. The methods include delivering a neurologic enhancing effective amount of a light energy having a wavelength in the visible to near-infrared wavelength range to at least one area of the brain of a subject. In a preferred embodiment delivering the neurologic function enhancing effective amount of light energy includes delivering a predetermined power density of light energy through the skull to the target area of the brain and/or delivering light energy through the skull to at least one area of the brain of a subject, wherein the wavelength, power density and amount of the light energy delivered are sufficient to cause an enhancement of neurologic functioning.

In accordance with one embodiment there is provided a method for preventing heat stroke in a subject. The term "preventing" in this context includes reducing the severity of a later heat stroke in a subject that has undergone treatment, reducing the incidence of heat stroke in individuals who have undergone treatment, as well as reducing the likelihood of onset heat stroke in a subject that has undergone treatment. The method includes delivering light energy having a wavelength in the visible to near-infrared wavelength range through the skull to at least one area of the brain of a subject, wherein the wavelength, power density and amount of the light energy delivered are sufficient to prevent, reduce the severity, or reduce the incidence of heat stroke in the subject.

In preferred embodiments, the target area of the brain may be all of the brain or a specific area of the brain including, but not limited to, an area associated with a particular cognitive or motor function, an area exhibiting neurodegeneration, the cortex, and/or an area that has been affected by trauma. The subject may have a cognitive or motor impairment such as from neurodegeneration or the subject may be normal.

In one embodiment, the predetermined power density is a power density of at least about 0.01 mW/cm$^2$. The predetermined power density in preferred embodiments is typically selected from the range of about 0.01 mW/cm$^2$ to about 100 mW/cm$^2$, including from about 0.01 mW/cm$^2$ to about 15 mW/cm$^2$ and from about 2 mW/cm$^2$ to about 50 mW/cm$^2$. In some embodiments, power densities above or below these values may be used.

In preferred embodiments, the methods encompass using light energy having a wavelength of about 630 nm to about 904 nm, and in one embodiment the light energy has a wavelength of about 780 nm to about 840 nm. The light energy is preferably from a coherent source (i.e. a laser), but light from non-coherent sources may also be used.

In some preferred embodiments, the methods encompass placing a light source in contact with a region of skin that is either adjacent an area of the brain in which treatment is desired, contralateral to such area, or a combination of the foregoing, and then administering the light energy, including the neurologic function enhancing effective amount of light energy, as may be measured by power density, to the area of the brain. In delivering the light, the power density may be a predetermined power density. Some preferred methods encompass determining a surface power density of the light energy sufficient for the light energy to penetrate the skull. The determination of the required surface power density, which is relatively higher than the power density to be delivered to the brain tissue being treated, takes into account factors that attenuate power density as it travels through tissue, including skin pigmentation, and location of the brain area being treated, particularly the distance of the brain area from the skin surface where the light energy is applied.

In accordance with another embodiment, there is provided a method of increasing the production of ATP by neurons to increase neurologic function. The method comprises irradiating neurons with light energy having a wavelength in the near infrared to visible portion of the electromagnetic spectrum for at least about 1 second, where the power density of said light energy at the neurons is at least about 0.01 mW/cm$^2$.

In accordance with another embodiment, there is provided a method for treating damage or illness in the central nervous system in a mammal or human, comprising delivering an effective amount of light energy to an in vitro culture comprising progenitor cells, and implanting the cells into the central nervous system of a mammal or human, wherein delivering an effective amount of light energy includes delivering light having a wavelength in the visible to near-infrared wavelength range and a power density of at least about 0.01 mW/cm$^2$ to the cells in culture.

DETAILED DESCRIPTION OF THE PREFERRED EMBODIMENTS

The low level light therapy methods for enhancing neurologic function and preventing, reducing the severity or reducing the incidence of heat stroke described herein may be practiced using, for example, a low level laser therapy apparatus such as that shown and described in U.S. Pat. Nos. 6,214,035, 6,267,780, 6,273,905 and 6,290,714, which are all herein incorporated by reference together with references contained therein.

Figure 1:
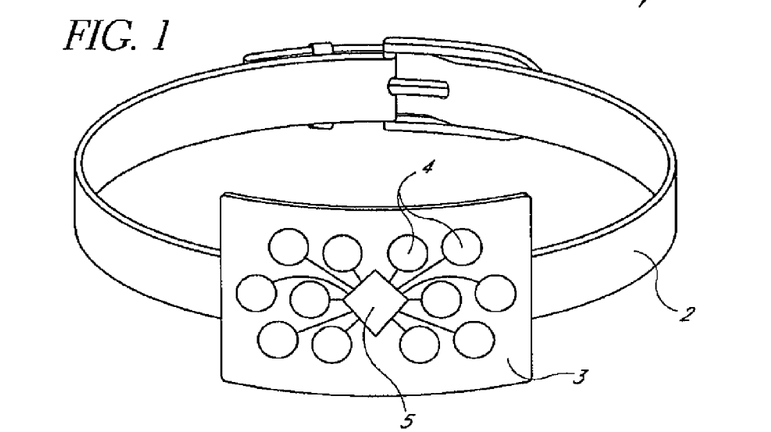
FIG. 1 is a perspective view of a first embodiment of a light therapy device.

Another suitable light therapy apparatus is that illustrated in FIG. 1. The illustrated device 1 includes a flexible strap 2 with a securing means, the strap adapted for securing the device over an area of the subject's body, one or more light energy sources 4 disposed on the strap 2 or on a plate or enlarged portion of the strap 3, capable of emitting light energy having a wavelength in the visible to near-infrared wavelength range, a power supply operatively coupled to the light source or sources, and a programmable controller 5 operatively coupled to the light source or sources and to the power supply. Based on the surprising discovery that control or selection of power density of light energy is an important factor in determining the efficacy of light energy therapy, the programmable controller is configured to select a predetermined surface power density of the light energy sufficient to deliver a predetermined subsurface power density to a body tissue to be treated beneath the skin surface of the area of the subject's body over which the device is secured.

The light energy source or sources are capable of emitting the light energy at a power sufficient to achieve the predetermined subsurface power density selected by the programmable controller. It is presently believed that tissue will be most effectively treated using subsurface power densities of light of at least about 0.01 mW/cm$^2$ and up to about 100 mW/cm$^2$, including about 0.05, 0.1, 0.5, 1, 5, 10, 15, 20, 30, 40, 50, 60, 70, 80, and 90 mW/cm$^2$. In one embodiment, power densities of about 20 mW/cm$^2$ to about 50 mW/cm$^2$ are used. To attain subsurface power densities within these stated ranges, taking into account attenuation of the energy as it travels through bone, body tissue, and fluids from the surface to the target tissue within the brain or on the surface of the brain, surface power densities of from about 100 mW/cm$^2$ to about 500 mW/cm$^2$ will typically be required, but also possibly to a maximum of about 1000 mW/cm$^2$. To achieve such surface power densities, preferred light energy sources, or light energy sources in combination, are capable of emitting light energy having a total power output of at least about 25 mW to about 500 mW, including about 30, 50, 75, 100, 150, 200, 250, 300, and 400 mW, but may also be up to a maximum of about 1000 mW. It is believed that the subsurface power densities of at least about 0.01 mW/cm$^2$ and up to about 100 mW/cm$^2$ in terms of the power density of energy that reaches the subsurface tissue are especially effective at producing the desired biostimulative effects on tissue being treated.

The strap is preferably fabricated from an elastomeric material to which is secured any suitable securing means, such as mating Velcro strips, snaps, hooks, buttons, ties, or the like. Alternatively, the strap is a loop of elastomeric material sized appropriately to fit snugly over a particular body part, such as a particular arm or leg joint, or around the chest or head. The precise configuration of the strap is subject only to the limitation that the strap is capable of maintaining the light energy sources in a select position relative to the particular area of the body or tissue being treated. In an alternative embodiment, a strap is not used and instead the light source or sources are incorporated into or attachable onto a light cap which fits securely over the head thereby holding the light source or sources in proximity to the patient's head for treatment. The light cap is preferably constructed of a stretchable fabric or mesh comprising materials such as Lycra or nylon. The light source or sources are preferably removably attached to the cap so that they may be placed in the position needed for treatment of any portion of the brain.

In the exemplary embodiment illustrated in FIG. 1, a light therapy device includes a flexible strap and securing means such as mating Velcro strips configured to secure the device around the head of the subject. The light source or sources are disposed on the strap, and in one embodiment are enclosed in a housing secured to the strap. Alternatively, the light source or sources are embedded in a layer of flexible plastic or fabric that is secured to the strap. In any case, the light sources are secured to the strap so that when the strap is positioned around a body part of the patient, the light sources are positioned so that light energy emitted by the light sources is directed toward the skin surface over which the device is secured. Various strap configurations and spatial distributions of the light energy sources are contemplated so that the device can be adapted to treat different tissues in different areas of the body.

Figure 2:
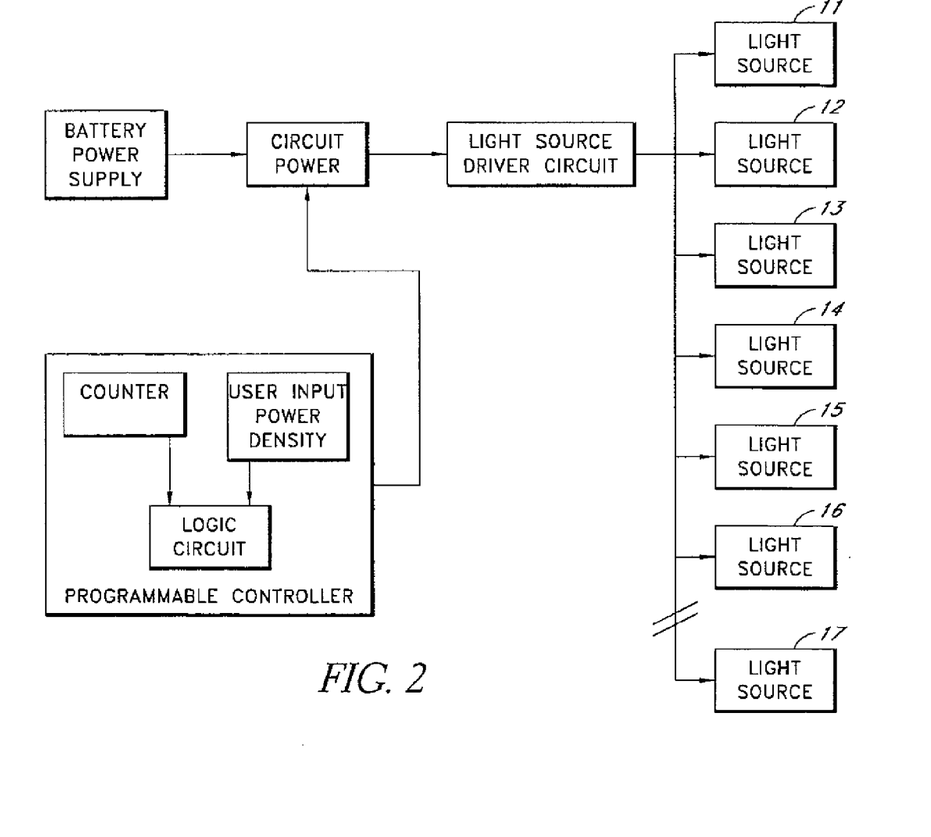
FIG. 2 is a block diagram of a control circuit for the light therapy device, according to one embodiment of the invention.

FIG. 2 is a block diagram of a control circuit according to one embodiment of the light therapy device. The programmable controller is configured to select a predetermined surface power density of the light energy sufficient to deliver a predetermined subsurface power density, preferably about 0.01 mW/cm$^2$ to about 100 mW/cm$^2$, including about 0.01 mW/cm$^2$ to about 15 mW/cm$^2$ and about 20 mW/cm$^2$ to about 50 mW/cm$^2$ to the infarcted area of the brain. The actual total power output if the light energy sources is variable using the programmable controller so that the power of the light energy emitted can be adjusted in accordance with required surface power energy calculations as described below.

Suitable for the methods described herein is a low level light apparatus including a handheld probe for delivering the light energy. The probe includes a light source of light energy having a wavelength in the visible to near-infrared wavelength range, i.e., from about 630 to about 904 nm, preferably about 780 nm to about 840 nm, including about 790, 800, 810, 820, and 830 nm. Preferred probes include, for example, a single source or laser diode that provides about 25 mW to about 500 mW of total power output, and multiple sources or laser diodes that together are capable of providing at least about 25 mW to about 500 mW of total power output. Probes and sources having power capacities outside of these limits may also be used in the methods according to preferred embodiments. The actual power output is variable using a control unit electronically coupled to the probe, so that power of the light energy emitted can be adjusted in accordance with required power density calculations as described below. In one embodiment, the diodes used are continuously emitting GaAlAs laser diodes having a wavelength of about 830 nm. In another embodiment, a laser source is used having a wavelength of about 808 nm. It has also been found that an intermediate wavelength of about 739 nm appears to be suitable for penetrating the skull, although other wavelengths are also suitable and may also be used.

Other preferred devices for use with the methods disclosed herein include those disclosed in U.S. patent application Ser. No. 10/682,379, filed Oct. 9, 2003, which is incorporated by reference in its entirety. For example, the light source is capable of emitting light energy at a power sufficient to achieve a predetermined power density at the subdermal target tissue (e.g., at a depth of approximately 2 centimeters from the dura). Taking into account the attenuation of energy as it propagates from the skin surface, through body tissue, bone, and fluids, to the subdermal target tissue, surface power densities preferably between about 10 mW/cm$^2$ to about 10 W/cm$^2$, or more preferably between about 100 mW/cm$^2$ to about 500 mW/cm$^2$, will typically be used to attain the selected power densities at the subdermal target tissue.

Preferred methods are based at least in part on the finding that given a select wave of light energy it is the power density of the light energy (i.e., light intensity or power per unit area, in W/cm$^2$) delivered to tissue, and not the power of the light source used nor the dosage of the energy used per se, that appears to be an important factor in determining the relative efficacy of low level light therapy. In the methods described herein, power density as delivered to a target area of the brain appears to be an important factor in using low level light therapy to achieve the desired clinical results. Without being bound by theory, it is believed that light energy delivered within a certain range of power densities provides the required biostimulative effect on the intracellular environment, such that the function of previously nonfunctioning or poorly functioning mitochondria in neurons is enhanced so as to return to a more normal state and the functioning of normally functioning mitochondria in neurons is enhanced to achieve better than normal functioning as well as to help the tissue be more resistant to the effects of excessive heat so as to prevent heat stroke or at least to reduce its incidence or severity.

The term "neurodegeneration" refers to the process of cell destruction resulting from primary destructive events such as stroke or trauma, and also secondary, delayed and progressive destructive mechanisms that are invoked by cells due to the occurrence of the primary destructive event. Primary destructive events include disease processes or physical injury or insult, including stroke, but also include other diseases and conditions such as multiple sclerosis, amylotrophic lateral sclerosis, heat stroke, epilepsy, Alzheimer's disease, dementia resulting from other causes such as AIDS, cerebral ischemia including focal cerebral ischemia, and physical trauma such as crush or compression injury in the CNS, including a crush or compression injury of the brain, spinal cord, nerves or retina, or any acute injury or insult producing neurodegeneration. Secondary destructive mechanisms include any mechanism that leads to the generation and release of neurotoxic molecules, including apoptosis, depletion of cellular energy stores because of changes in mitochondrial membrane permeability, release or failure in the reuptake of excessive glutamate, reperfusion injury, and activity of cytokines and inflammation. Both primary and secondary mechanisms may contribute to forming a "zone of danger" for neurons, wherein the neurons in the zone have at least temporarily survived the primary destructive event, but are at risk of dying due to processes having delayed effect.

The term "neuroprotection" refers to a therapeutic strategy for slowing or preventing the otherwise irreversible loss of neurons due to neurodegeneration after a primary destructive event, whether the neurodegeneration loss is due to disease mechanisms associated with the primary destructive event or secondary destructive mechanisms.

The term "cognitive function" as used herein refers to cognition and cognitive or mental processes or functions, including those relating to knowing, thinking, learning, perception, memory, and judging. Diseases or conditions affecting cognitive function include Alzheimer's disease, dementia, head trauma, stroke, depression and other mental diseases which cause disruption in cognitive function, and neurodegeneration.

The term "motor function" as used herein refers to those bodily functions relating to muscular movements, primarily conscious muscular movements, including motor coordination, performance of simple and complex motor acts, and the like.

The term "neurologic function" as used herein includes both cognitive function and motor function.

The terms "cognitive enhancement" and "motor enhancement" as used herein refer to the improving or heightening of cognitive function and motor function, respectively.

The term "neurologic enhancement" as used herein includes both cognitive enhancement and motor enhancement.

The term "neuroprotective effective" as used herein refers to a characteristic of an amount of light energy, wherein the amount is a power density of the light energy measured in mW/cm$^2$. The amount of light energy achieves the goal of preventing, avoiding, reducing or eliminating neurodegeneration, which should result in cognitive enhancement and/or motor enhancement.

The term "neurologic function enhancement effective" as used herein refers to a characteristic of an amount of light energy, wherein the amount is a power density of the light energy measured in mW/cm$^2$. The amount of light energy achieves the goal of neuroprotection, motor enhancement and/or cognitive enhancement.

Thus, a method for the enhancement of neurologic function in a subject involves delivering a neurologic function enhancement effective amount of light energy having a wavelength in the visible to near-infrared wavelength range to a target area of the brain of the subject. In a preferred embodiment, delivering the neurologic function enhancement effective amount of light energy includes selecting a surface power density of the light energy sufficient to deliver such predetermined power density of light energy to the target area of the brain. Likewise, a method for preventing, reducing the severity of a later heat stroke in a subject, reducing the incidence of future heat stroke, and/or reducing the likelihood of onset heat stroke in a subject includes delivering light energy having a wavelength in the visible to near-infrared wavelength range and a predetermined power density through the skull to at least one area of the brain of a subject, wherein the wavelength, power density and amount of the light energy delivered are sufficient to prevent, reduce the severity, or reduce the incidence of heat stroke in the subject.

Preferably, the predetermined power density to be delivered to the tissue in accordance with the above methods is selected to be at least about 0.01 mW/cm$^2$. In one embodiment, the predetermined power density is selected from the range of about 0.01 mW/cm$^2$ to about 100 mW/cm$^2$. To deliver the predetermined power density at the level of the brain tissue, a required, relatively greater surface power density of the light energy is calculated taking into account attenuation of the light energy as it travels from the skin surface through various tissues including skin, bone and brain tissue. Factors known to affect penetration and to be taken into account in the calculation include skin pigmentation, the presence and color of hair over the area to be treated (if any), and the location of the affected brain region, particularly the depth of the area to be treated relative to the surface. For example, to obtain a desired power density of 50 mW/cm$^2$ in the brain at a depth of 3 cm below the surface may require a surface power density of 500 mW/cm$^2$. The higher the level of skin pigmentation, the higher the required surface power density to deliver a predetermined power density of light energy to a subsurface brain site. The light energy can have a predetermined power density at the subdermal target tissue (e.g., at a depth of approximately 2 centimeters below the dura). It is presently believed that phototherapy of tissue is most effective when irradiating the target tissue with power densities of light of at least about 0.01 mW/cm$^2$ and up to about 1 W/cm$^2$. In various embodiments, the subsurface power density is at least about 0.01, 0.05, 0.1, 0.5, 1, 5, 10, 15, 20, 30, 40, 50, 60, 70, 80, or 90 mW/cm$^2$, respectively, depending on the desired clinical performance. In certain embodiments, the subsurface power density is preferably about 0.01 mW/cm$^2$ to about 100 mW/cm$^2$, more preferably about 0.01 mW/cm$^2$ to about 50 mW/cm$^2$, and most preferably about 2 mW/cm$^2$ to about 20 mW/cm$^2$. It is believed that these subsurface power densities are especially effective at producing the desired biostimulative effects on the tissue being treated.

The wavelength of the light energy is selected from the range of about 630 nm to about 904 nm, and of course is dependent on the source of light energy used one embodiment, using light apparatus including GaAlAs laser diodes, the light energy has a wavelength of about 830 nm.

In preferred embodiments, the light source used in light therapy is a coherent source (i.e. a laser), and/or the light is substantially monochromatic (i.e. one wavelength or a very narrow band of wavelengths).

To treat a patient, including those suffering from neurodegeneration or a loss or diminishment of motor skills, cognition or cognitive or mental processes or functions, as well as persons having generally normal cognitive or motor functions (whether to enhance such functions or to pre-treat so as to prevent or lessen heat stroke), the light source is placed in contact with a region of skin, for example on the scalp, adjacent a target area of the brain. The target area may be an area of the brain affected by disease or trauma that has been identified such as by using standard medical imaging techniques, it may be a portion of the brain that is known to control certain functions or processes, or it may be any section of the brain, including but not limited to the cortex, cerebellum and other brain regions. Then a surface power density calculation is performed which takes into account factors including skull thickness of the patient, skin coloration, distance to the target site or affected site within the brain, etc. that affect penetration and thus power density at the target or affected site. The power and other parameters are then adjusted according to the results of the calculation.

The precise power density selected for treating the patient will depend on a number of factors, including the specific wavelength of light selected, the type of disease (if any), the clinical condition of the subject including the extent of brain area affected, and the like. Similarly, it should be understood that the power density of light energy to be delivered to the target area or affected brain area may be adjusted to be combined with any other therapeutic agent or agents, especially pharmaceutical agents to achieve the desired biological effect. The selected power density will again depend on a number of factors, including the specific light energy wavelength chosen, the individual additional therapeutic agent or agents chosen, and the clinical condition of the subject.

In preferred embodiments, the treatment proceeds continuously for a period of about 30 seconds to about 2 hours, more preferably for a period of about 1 to 20 minutes. The treatment may be terminated after one treatment period, or the treatment may be repeated with preferably about 1 to 2 days passing between treatments. The length of treatment time and frequency of treatment periods depends on several factors, including the functional recovery of the patient and the results of imaging analysis. In some cases, such as where the disease is degenerative (e.g. Alzheimer's disease) or where treatment is given to a generally healthy patient, the treatment may continue at chosen intervals indefinitely.

During the treatment, the light energy may be continuously provided, or it may be pulsed. If the light is pulsed, the pulses are preferably at least about 10 ns long and occur at a frequency of up to about 100 Hz. Continuous wave light may also be used.

It has been discovered that treatment of stroke using low level light therapy is more effective if treatment begins several hours after the stroke has occurred. This is a surprising result, in that the thrombolytic therapies currently in use for treatment of stroke must begin within a few hours of the stroke. Because oftentimes many hours pass before a person who has suffered a stroke receives medical treatment, the short time limit for initiating thrombolytic therapy excludes many patients from treatment. Consequently, the present methods may be used to treat a greater percentage of stroke patients. Accordingly, it is believed that treatment to enhance cognitive and/or motor function may also take place after a primary event occurs in that it appears that the neural cells need only be living to receive benefit from the methods described herein.

EXAMPLE

An in vitro experiment was done to demonstrate one effect of light therapy on neurons, namely the effect on ATP production. Normal Human Neural Progenitor (NHNP) cells were obtained cryopreserved through Clonetics (Baltimore, Md.), catalog #CC-2599. NHNP cells were thawed and cultured on polyethyleneimine (PEI) with reagents provided with the cells, following the manufacturers instructions. The cells were plated into 96 well plates (black plastic with clear bottoms, Becton Dickinson, Franklin Lakes N.J.) as spheroids and allowed to differentiate into mature neurons over a period of two weeks.

A Photo Dosing Assembly (PDA) was used to provide precisely metered doses of laser light to the NHNP cells in the 96 well plate. The PDA comprised a Nikon Diaphot inverted microscope (Nikon, Melville, N.Y.) with a LUDL motorized x,y,z stage (Ludl Electronic Products, Hawthorne, N.Y.). An 808 nm laser was routed into the rear epi-fluorescent port on the microscope using a custom designed adapter and a fiber optic cable. Diffusing lenses were mounted in the path of the beam to create a "speckled" pattern, which was intended to mimic in vivo conditions after a laser beam passed through human skin. The beam diverged to a 25 mm diameter circle when it reached the bottom of the 96 well plate. This dimension was chosen so that a cluster of four adjacent wells could be lased at the same time. Cells were plated in a pattern such that a total of 12 clusters could be lased per 96 well plate. Stage positioning was controlled by a Silicon Graphics workstation and laser timing was performed by hand using a digital timer. The measured power density passing through the plate for the NHNP cells was 50 mW/cm$^2$.

Two independent assays were used to measure the effects of 808 nm laser light on the NHNP cells. The first was the CellTiter-Glo Luminescent Cell Viability Assay (Promega, Madison, Wis.). This assay generates a "glow-type" luminescent signal produced by a luciferase reaction with cellular ATP. The CellTiter-Glo reagent is added in an amount equal to the volume of media in the well and results in cell lysis followed by a sustained luminescent reaction that was measured using a Reporter luminometer (Turner Biosystems, Sunnyvale, Calif.). Amounts of ATP present in the NHNP cells were quantified in Relative Luminescent Units (RLUs) by the luminometer.

The second assay used was the alamarBlue assay (Biosource, Camarillo, Calif.). The internal environment of a proliferating cell is more reduced than that of a non-proliferating cell. Specifically, the ratios of NADPH/NADP, FADH/FAD, FMNH/FMN and NADH/NAD, increase during proliferation. Laser irradiation is also thought to have an effect on these ratios. Compounds such as alamarBlue are reduced by these metabolic intermediates and can be used to monitor cellular states. The oxidization of alamarBlue is accompanied by a measurable shift in color. In its unoxidized state, alamarBlue appears blue; when oxidized, the color changes to red. To quantify this shift, a 340PC microplate reading spectrophotometer (Molecular Devices, Sunnyvale, Calif.) was used to measure the absorbance of a well containing NHNP cells, media and alamarBlue diluted 10% v/v. The absorbance of each well was measured at 570 nm and 600 nm and the percent reduction of alamarBlue was calculated using an equation provided by the manufacturer.

The two metrics described above, (RLUs and % Reduction) were then used to compare NHNP culture wells that had been lased with 50 mW/cm$^2$ at a wavelength of 808 nm. For the CellTiter-Glo assay, 20 wells were lased for 1 second and compared to an unlased control group of 20 wells. The CellTiter-Glo reagent was added 10 min after lasing completed and the plate was read after the cells had lysed and the luciferase reaction had stabilized. The average RLUs measured for the control wells was 3808+/−3394 while the laser group showed a two fold increase in ATP content to 7513+/−6109. The standard deviations were somewhat high due to the relatively small number of NHNP cells in the wells (approximately 100 per well from visual observation), but a student's unpaired t-test was performed on the data with a resulting p-value of 0.02 indicating that the twofold change is statistically significant.

The alamarBlue assay was performed with a higher cell density and a lasing time of 5 seconds. The plating density (calculated to be between 7,500-26,000 cells per well based on the certificate of analysis provided by the manufacturer) was difficult to determine since some of the cells had remained in the spheroids and had not completely differentiated. Wells from the same plate can still be compared though, since plating conditions were identical. alamarBlue was added immediately after lasing and the absorbance was measured 9.5 hours later. The average measured values for percent reduction were 22%+/−7.3% for the 8 lased wells and 12.4%+/−5.9% for the 3 unlased control wells (p-value=0.076). These alamarBlue results support the earlier findings in that they show a similar positive effect of the laser treatment on the cells.

Increases in cellular ATP concentration and a more reduced state within the cell are both related to cellular metabolism and are considered to be indications that the cell is viable and healthy. These results are novel and significant in that they show the positive effects of laser irradiation on cellular metabolism in in-vitro neuronal cell cultures.

In one embodiment, treatment of a patient includes implantation of progenitor cells into the central nervous system ("CNS") of the patient. Following implantation, the progenitor cells differentiate to form one or more cell types of the central nervous system. The implanted cells may serve any of a variety of purposes, including replacement of cells or tissues that have been irreparably damaged, repair of a portion of the CNS, enhance the production of important CNS neurochemicals such as dopamine, seratonin, endogenous opioid peptides, and the like. Implantation of progenitor cells may be performed alone, or it may be done in combination with the methods of enhancing neurologic functioning, as described herein.

The term "progenitor cell" as used herein refers to either (1) a pluripotent, or lineage-uncommitted, progenitor cell, a "stem cell" or "mesenchymal stem cell", that is potentially capable of an unlimited number of mitotic divisions to either renew its line or to produce progeny cells that will differentiate into any of a variety of cells, including cells of the central nervous system including neural cells such as astrocytes, oligodendrocytes, and neurons; or (2) a lineage-committed progenitor cell produced from the mitotic division of a stem cell which will eventually differentiate into a neural cell.

Unlike the stem cell from which it is derived, the lineage-committed progenitor is generally considered to be incapable of an unlimited number of mitotic divisions and will eventually differentiate into a neural cell or other CNS cell.

The term "differentiation" as used herein refers to the process whereby an unspecialized, pluripotent stem cell proceeds through one or more intermediate stage cellular divisions, ultimately producing one or more specialized cell types. Differentiation thus includes the process whereby precursor cells, i.e. uncommitted cell types that precede the fully differentiated forms but may or may not be true stem cells, proceed through intermediate stage cell divisions to ultimately produce specialized cell types. Differentiation encompasses the process whereby mesenchymal stem cells (MSC) are induced to differentiate into one or more of the committed cell types comprising the central nervous system, in vivo or in vitro.

The terms "growth chamber" and "cell culture chamber" as used herein are used interchangeably and are to be interpreted very broadly to refer to any container or vessel suitable for culturing cells, including, but not limited to, dishes, culture plates (single or multiple well), bioreactors, incubators, and the like. In one embodiment, a cell culture apparatus such as is described in copending U.S. application Ser. No. 10/700,355, filed Nov. 3, 2003 is used. This application is hereby incorporated by reference herein in its entirety.

In a preferred culture method, progenitor cells are inoculated and grown in a cell culture in vitro, using preferred parameters including power density as discussed above. Because the light energy is applied directly to the cell culture in vitro and does not travel through intervening body tissue, the power density selected to be delivered to the cell is generally equal to the power density of the light energy as it is emitted from the light apparatus. If lenses, filters, dispersion gratings, or any other material lies between the light source and the cells, any absorption or dispersion of the light energy by such material should be taken into account and the applied light energy adjusted, if needed, to account for the material. In one embodiment, the treated cells are implanted following treatment. In another embodiment, at least some treated cells remain in culture to maintain the cell line for later use.

After in vitro treatment of cells using electromagnetic energy, the cells are transplanted or implanted to a recipient site in a patient. In one embodiment, the treatment prior to transplantation or implantation includes culturing cells sufficient for implantation. The recipient site may be a site of injury, illness, or defect, or it may be a region of relatively healthy tissue. In some embodiments, the recipient site and/or the region surrounding such site is treated with light energy according to the methods described supra, before and/or after implantation to enhance the rate at which the implanted cells are integrated with surrounding tissue at the recipient site.

In one embodiment, progenitor cells such as stem cells are treated with electromagnetic energy as noted above and then implanted into the brain of a patient, such a patient who is at risk for Parkinson's disease, exhibits symptoms of Parkinson's disease, and/or has been diagnosed with Parkinson's disease. Following implantation, the recipient site is optionally treated with electromagnetic energy, including directly at the recipient site or through the skull at the recipient site, or some other portion of the brain, such as the cortex. The transplanted cells produce dopamine to treat, or lessen the symptoms and/or delay onset of Parkinson's disease in the patient.

In another embodiment, progenitor cells are treated with electromagnetic energy and implanted or transplanted at a site of physical trauma to the spinal cord or one or more nerves of a patient. Following implantation, the recipient site is optionally treated with electromagnetic energy. Such optional treatment may include treatment immediately following implantation and/or one or more treatment periods following implantation. The transplanted cells help repair damage to the spinal cord or nerve(s) such that the recovery or prognosis is enhanced in patients having implanted progenitor cells as compared with those who do not receive such implants.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. A method for treating a subject having a loss of neurologic function caused by Alzheimer's disease, the method comprising:
   identifying a subject having a loss of neurologic function caused by Alzheimer's disease;
   noninvasively delivering light energy having a wavelength of about 630 nanometers to about 904 nanometers to the brain of the subject,
   wherein delivering the light energy comprises irradiating the scalp with light energy having an incident power density less than about 1000 mW/cm$^2$ for a time period of about 30 seconds to about 20 minutes such that a portion of the light energy is transmitted through the scalp and the skull to the brain.

2. The method of claim 1, wherein the light energy has a wavelength of about 780 nanometers to about 840 nanometers.

3. The method of claim 1, wherein the incident power density is greater than about 500 mW/cm$^2$.

4. The method of claim 1, wherein the transmitted portion of the light energy has a power density in the range of about 0.01 mW/cm$^2$ to about 100 mW/cm$^2$ at a depth of approximately 2 centimeters below the dura.

5. The method of claim 1, wherein the transmitted portion of the light energy has a power density in the range of about 0.01 mW/cm$^2$ to about 15 mW/cm$^2$ at a depth of approximately 2 centimeters below the dura.

6. The method of claim 1, wherein delivering the light energy comprises placing a light source in contact with the scalp.

7. The method of claim 1, wherein the light energy is pulsed.

8. The method of claim 1, wherein the neurologic function of the subject is enhanced after the irradiation the scalp as compared to the neurologic function of the subject prior to the irradiation.

9. The method of claim 1, wherein the loss of neurologic function comprises a loss of motor function.

10. The method of claim 1, wherein the loss of neurologic function comprises cognitive impairment.

11. The method of claim 1, wherein the loss of neurologic function comprises dementia.

* * * * *